US009656979B2

(12) United States Patent
Vath

(10) Patent No.: US 9,656,979 B2
(45) Date of Patent: May 23, 2017

(54) METHODS OF TREATING AN OVERWEIGHT OR OBESE SUBJECT

(71) Applicant: Zafgen, Inc., Boston, MA (US)

(72) Inventor: James E. Vath, Lynnfield, MA (US)

(73) Assignee: Zafgen, Inc., Boston, MA (US)

(*) Notice: Subject to any disclaimer, the term of this patent is extended or adjusted under 35 U.S.C. 154(b) by 0 days.

(21) Appl. No.: 14/616,002

(22) Filed: Feb. 6, 2015

(65) Prior Publication Data
US 2015/0150857 A1 Jun. 4, 2015

Related U.S. Application Data

(63) Continuation of application No. 13/133,062, filed as application No. PCT/US2009/066809 on Dec. 4, 2009, now abandoned.

(60) Provisional application No. 61/260,194, filed on Nov. 11, 2009, provisional application No. 61/275,688, filed on Aug. 3, 2009, provisional application No. 61/119,881, filed on Dec. 4, 2008, provisional application No. 61/119,875, filed on Dec. 4, 2008, provisional application No. 61/119,884, filed on Dec. 4, 2008, provisional application No. 61/119,886, filed on Dec. 4, 2008.

(51) Int. Cl.
| | | |
|---|---|---|
| C07D 303/06 | (2006.01) |
| C07D 405/14 | (2006.01) |
| C07D 453/02 | (2006.01) |
| A61K 31/336 | (2006.01) |
| A61K 31/439 | (2006.01) |
| A61K 31/4025 | (2006.01) |
| C07D 303/22 | (2006.01) |
| C07D 303/10 | (2006.01) |
| C07D 405/12 | (2006.01) |

(52) U.S. Cl.
CPC .......... *C07D 303/22* (2013.01); *A61K 31/336* (2013.01); *A61K 31/4025* (2013.01); *A61K 31/439* (2013.01); *C07D 303/06* (2013.01); *C07D 303/10* (2013.01); *C07D 405/12* (2013.01); *C07D 453/02* (2013.01); *Y10S 514/909* (2013.01)

(58) Field of Classification Search
None
See application file for complete search history.

(56) References Cited

U.S. PATENT DOCUMENTS

| | | | |
|---|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,989,392 B2 | 1/2006 | Collins et al. |
| 7,084,108 B2 | 8/2006 | Olson et al. |
| 7,268,111 B2 | 9/2007 | Olson et al. |
| 7,718,695 B2 | 5/2010 | Kim et al. |
| 8,367,721 B2 | 2/2013 | Hughes et al. |
| 8,642,650 B2 | 2/2014 | Hughes et al. |
| 8,865,746 B2 | 10/2014 | Vath |
| 8,980,946 B2 | 3/2015 | Hughes |
| 9,000,035 B2 | 4/2015 | Hughes |

(Continued)

FOREIGN PATENT DOCUMENTS

| | | |
|---|---|---|
| EP | 0357061 A1 * | 7/1990 |
| EP | 0682020 A1 | 11/1995 |

(Continued)

OTHER PUBLICATIONS

Festi et al., Obesity Reviews, 2004, vol. 5, pp. 27-42.*
Anderson, H. H., The Use of Fumagillin in Amoebiasis. Annals of the New York Academy of Sciences, 55:1118-1124, Dec. 30, 1952.
Benny et al., "An Orally Delivered Small-Molecule Formulation with Antiangiogenic and Anticancer Activity" Nat Biotechnol. Jul. 2008;26(7):799-807.
Bernier et al. "Fumagillin class inhibitors of methionine aminopeptidase-2" Drugs of the Future 30(5):497-500, 2005.
Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.
Braunwald et al, "Obesity" in Harrison's Principles of Internal Medicine, 15th Ed., McGraw Hill (New York) pp. 479-486, 2001.
Chun et al. "Novel inhibitors targeted to methionine aminopeptidase 2 (MetAP2) strongly inhibit the growth of cancers in xenografted nude model" Int J Cancer. Mar. 10, 2005;114(1):124-30.

(Continued)

*Primary Examiner* — Savitha Rao
*Assistant Examiner* — Gregg Polansky
(74) *Attorney, Agent, or Firm* — Goodwin Proctor LLP

(57) ABSTRACT

The disclosure herein generally relates to methods of treating an overweight or obese condition, and overweight or obesity-related conditions. In one embodiment, the disclosure provides a method of treating an overweight or obese condition involving administering to the subject in need thereof, an amount of a pharmaceutical composition including a MetAp-2 inhibitory compound, or a salt, ester, or prodrug thereof, effective to result in weight loss in the subject.

7 Claims, 1 Drawing Sheet

(56) References Cited

U.S. PATENT DOCUMENTS

| | | |
|---|---|---|
| 9,173,865 B2 | 11/2015 | Hughes |
| 2004/0067266 A1 | 4/2004 | Toppo |
| 2004/0116495 A1 | 6/2004 | Marino Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |
| 2014/0011870 A1 | 1/2014 | Hughes |
| 2015/0150840 A1 | 6/2015 | Vath |
| 2015/0209320 A1 | 7/2015 | Hughes et al. |
| 2015/0209321 A1 | 7/2015 | Hughes |
| 2015/0335608 A1 | 11/2015 | Hughes et al. |
| 2015/0361061 A1 | 12/2015 | Vath |

FOREIGN PATENT DOCUMENTS

| | | |
|---|---|---|
| WO | WO-99/59986 A1 | 11/1999 |
| WO | WO-99/59987 A1 | 11/1999 |
| WO | WO-00/64876 A1 | 11/2000 |
| WO | WO-03/027104 A1 | 4/2003 |
| WO | WO-2004/033419 A1 | 4/2004 |
| WO | WO-2005/082349 A1 | 9/2005 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/051318 A1 | 4/2012 |
| WO | WO-2012/064838 A1 | 5/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |

OTHER PUBLICATIONS

Didier et al. "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo et al. "Studies on the Carcinolytic Activity of Fumagillin and Some of its Derivatives," Antibiot Annu.1958-1959;6:541-6.

Drevs et al. "Antiangiogenic Potency of FK866/K22.175, a New Inhibitor of Intracellular NAD Biosynthesis, in Murine Renal Cell Carcinoma" Anticancer Res. Nov.-Dec. 2003;23(6C):4853-8.

Dumas et al., "Synthesis and Structure Activity Relationships of Novel Small Molecule Cathepsin D Inhibitors" Bioorg Med Chem Lett. Sep. 6, 1999;9(17):2531-6.

Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.").

European Search Report for EP 09798793 dated Oct. 11, 2011, 9 pages.

Everhart "Contributions of Obesity and Weight Loss to Gallstone Disease" Ann Intern Med. Nov. 15, 1993;119(10):1029-35.

Garrabrant et al. "Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

Han et al. "Design and Synthesis of Highly Potent Fumagillin Analogues from Homology Modeling for a Human MetAP-2" Bioorg Med Chem Lett. Jan. 3, 2000;10(1):39-43.

Ingber et al. "Synthetic analogues of fumagillin that inhibit angiogenesis and suppress tumour growth" Nature. Dec. 6, 1990;348(6301):555-7.

International Search Report for International Application No. PCT/US2011/38352, International Filing Date May 27, 2011,3 pages.

International Search Report for International Application PCT/US2010/052050, dated Mar. 25, 2011, 3 pages.

Jeong et al, "Total synthesis and antiangiogenic activity of cyclopentane analogues of fumagillol" Bioorg Med Chem Lett. Aug. 1, 2005;15(15):3580-3.

Kim et al. "Assessment of the Anti-Obesity Effects of the TNP-470 Analog, CKD-732" J Mol Endocrinol. Apr. 2007;38(4):455-65.

Kim et al. "Development of parenteral formulation for a novel angiogenesis inhibitor, CKD-732 through complexation with hydroxwropyl-beta-cyclodextrin" Int J Pharm. Mar. 19, 2004;272(1-2):79-89.

Kim et al. "General pharmacology of CKD-732, a new anticancer agent: effects on central nervous, cardiovascular, and respiratory system" Biol Pharm Bull. Feb. 2005;28(2):217-23.

Kruger, "TNP-470: An Angiogenesis Inhibitor in Clinical Development for Cancer" Expert Opin Investig Drugs. Jun. 2000;9(6):1383-96.

Lee et al. "Absorption, distribution, metabolism, and excretion of CKD-732, a novel antiangiogenic fumagillin derivative, in rats, mice, and dogs" Arch Pharm Res. Feb. 2004;27(2):265-72.

Lee et al. "Design, Synthesis, and Antiangiogenic Effects of a Series of Potent Novel Fumagillin Analogues" Chem Pharm Bull (Tokyo). Jul. 2007;55(7):1024-9.

Lee et al. "Selective N-demethylation of tertiary aminofumagillols with selenium dioxide via a non-classical Polonovski type reaction" Heterocycles 68(5):915-932, 2006.

Lijnen et al. "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.

Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.

McCowen et al., "Fumagillin (H-3), a New Antibiotic with Amebicidal Properties" Science. Feb. 23, 1951;113(2930):202-3.

Milkowski et al., "TNP-470" Antiangiogenic Agents in Cancer Therapy, Chapter 22 pp. 385-398, 1999.

Molina et al. "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.

Molina et al. "Fumagillin Treatment of Intestinal Microsporidiosis" N Engl J Med. Jun. 20, 2002;346(25):1963-9.

Molina, et al. "Trial of Oral Fumagillin for the Treatment of Intestinal Microsporidiosis in Patients with HIV Infection" AIDS. Jul. 7, 2000;14(10):1341-8.

Myung et al. "The identification of in vitro metabolites of CKD-732 by liquid chromatography/tandem mass spectrometry" Rapid Commun Mass Spectrom. 2002;16(21):2048-53.

Naganuma et al. "Metronomic doxifluridine chemotherapy combined with the anti-angiogenic agent TNP-470 inhibits the growth

(56) References Cited

OTHER PUBLICATIONS of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA Aug. 25, 1993;270(8):967-74.
Noel et al. "Increased Risk of Acute Pancreatitis and Biliary Disease Observed in Patients with Type 2 Diabetes "Diabetes Care. May 2009;32(5):834-8. doi: 10.2337/dc08-1755. Epub Feb. 10, 2009.
Pagliarulo et al. "Gallstone disease and related risk factors in a large cohort of diabetic patients" Dig Liver Dis. Feb. 2004;36(2):130-4.
Picoul et al. "Progress in fumagillin synthesis" Pure Appl. Chem. 75(2-3): 235-249, 2003.
Rhee et al. "Angiogenesis inhibitor attenuates parathyroid hormone-induced anabolic effect" Biomed Pharmacother. Jan. 2009;63(1):63-8. doi: 10.1016/j.biopha.2007.10.013. Epub Nov. 20, 2007.
Rupnick "Adipose Tissue Mass Can be Regulated Through the Vasculature" Proc Natl Acad Sci U.S.A. Aug. 6, 2002;99(16):10730-5. Epub Jul. 29, 2002.
Seneca et al. "Amebiasis: a review. II. Laboratory diagnosis, differential diagnosis and therapy" Am J Dig Dis. Jul. 1956;1(7):310-22.
Shin et al. "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy" Invest New Drugs. Apr. 2012;30(2):672-80.
Shin et al., "A Phase I Pharmacokinetic and Pharmacodynamic Study of CKD-732, an Antiangiogenic Agent, in Patients with Refractory Solid Cancer". Invest New Drugs. Oct. 2010;28(5):650-8.
Srikumar et al. "Structural insights on Brugia malayi transglutaminase with cinnamoyl derivatives—a molecular docking approach" International Journal of Pharma and Bio Sciences 3(3):998-1006, 2012.
Teicher et al., "Antiangiogenic Agents in Cancer Therapy" pp. 385-398, 1999.
Weinsier et al. "Gallstone Formation and Weight Loss" Obes Res. Jan. 1993;1(1):51-6.
Weinsier et al. "Medically Safe Rate of Weight Loss for the Treatment of Obesity: A Guideline Based on Risk of Gallstone Formation" Am J Med. Feb. 1995;98(2):115-7.
Winter et al. "Endothelial anb3 Integrin-Targeted Fumagillin Nanoparticles Inhibit Angiogenesis in Atherosclerosis" Arterioscler Thromb Vasc Biol. Sep. 2006;26(9):2103-9. Epub Jul. 6, 2006.
Yanai et al. "Antitumor Effect of Arterial Administration of a Medium-Chain Triglyceride Solutionof an Angiogenesis Inhibitor, TNP-470, in Rabbits Bearing VX-2 Carcinoma" Pharm Res. May 1995;12(5):653-7.
Yanai et al., "Antitumor activity of a medium-chain triglyceride solution of the angiogenesis inhibitor TNP-470 (AGM-1470) when administered via the hepatic artery to rats bearing Walker 256 carcinosarcoma in the liver" J Pharmacol Exp Ther. Dec. 1994;271(3):1267-73.

* cited by examiner

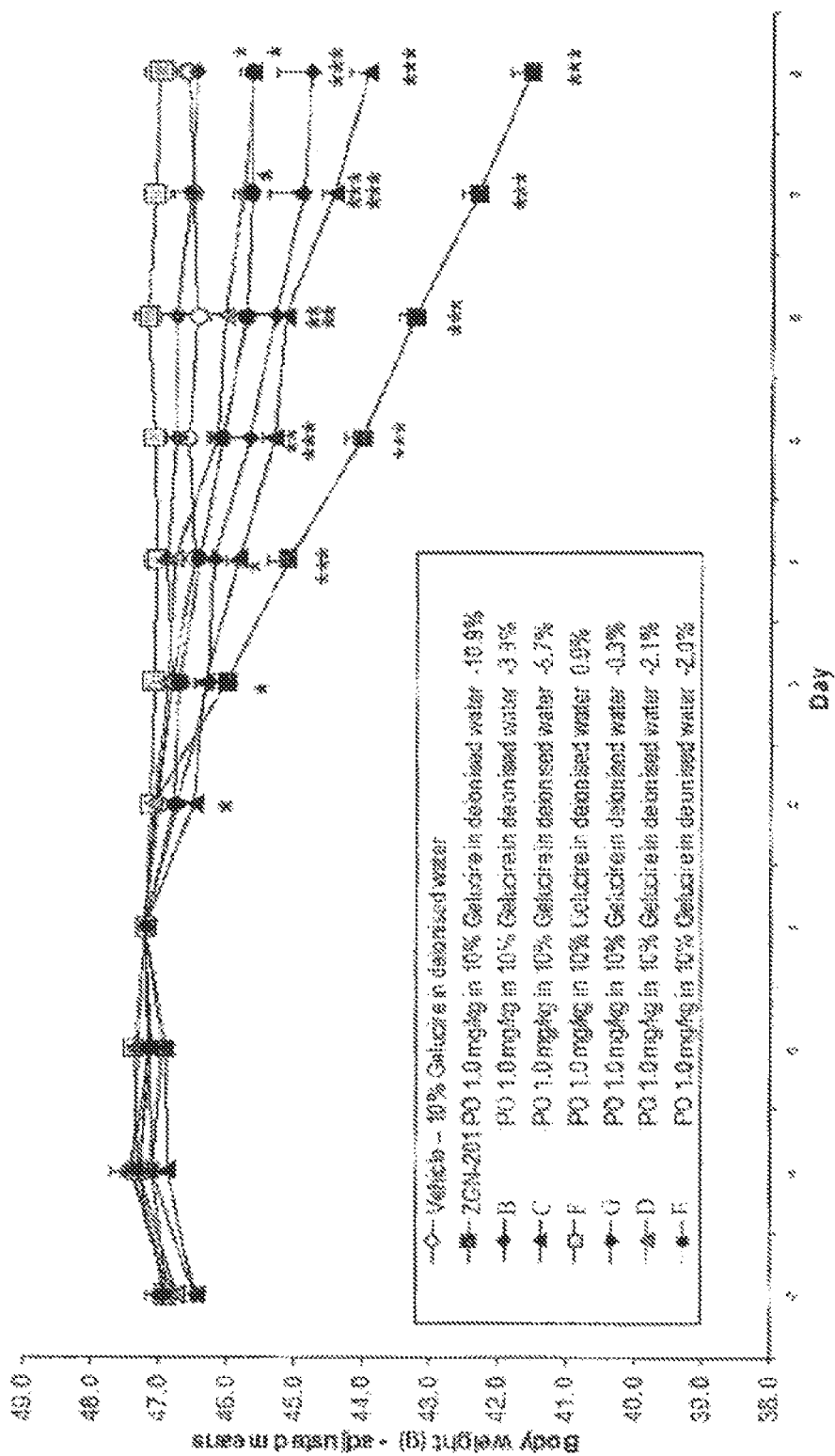

METHODS OF TREATING AN OVERWEIGHT OR OBESE SUBJECT

REFERENCE TO RELATED APPLICATIONS

This application is a continuation of U.S. Ser. No. 13/133,062, field Sep. 22, 2011, which is a national stage filing under 35 U.S.C. §371 of PCT/US2009/066809, filed Dec. 4, 2009, which claims priority to U.S. provisional applications U.S. Ser. No. 61/119,875 filed Dec. 4, 2008, U.S. Ser. No. 61/119,881 filed Dec. 4, 2008, U.S. Ser. No.61/119,884 filed Dec. 4, 2008, U.S. Ser. No. 61/119,886 filed Dec. 4, 2008, U.S. Ser. No. 61/275,688 filed Aug. 3, 2009, and U.S. Ser. No. 61/260,194 filed Nov. 11, 2009, each application of which is hereby incorporated by reference.

BACKGROUND

Obesity is a complex medical disorder of appetite regulation, and metabolism resulting in excessive accumulation of adipose tissue mass. Typically defined as a body mass index (BMI) of 30 kg/m$^2$ or more, obesity is a world-wide public health concern that is associated with cardiovascular disease, diabetes, certain cancers, respiratory complications, osteoarthritis, gallbladder disease, decreased life expectancy, and work disability, The primary goals of obesity therapy are to reduce excess body weight, improve or prevent obesity-related morbidity and mortality, and maintain long-term weight loss.

Treatment modalities typically include lifestyle management, pharmacotherapy, and surgery. Treatment decisions are made based on severity of obesity, seriousness of associated medical conditions, patient risk status, and patient expectation. Notable improvements in cardiovascular risk and the incidence of diabetes have been observed with weight loss of 5-10% of body weight, supporting clinical guidelines for the treatment of obesity that recommend a target threshold of 10% reduction in body weight from baseline values.

However, while prescription anti-obesity medications are typically considered for selected subjects at increased medical risk because of their weight and for whom lifestyle modifications (diet restriction, physical activity, and behavior therapy) alone have failed to produce durable weight loss, approved drugs have had unsatisfactory efficacy for severely obese subjects, leading to only ~3-5% reduction, in body weight after a year of treatment.

Bariatric surgery may be considered as a weight loss intervention for subjects at or exceeding a BMI of 40 kg/m$^2$. Subjects with a BMI ≥35 kg/m$^2$ and an associated serious medical condition are also candidates for this treatment option. Unfortunately, postoperative complications commonly result from bariatric surgical procedures, including bleeding, embolism, or thrombosis, wound complications, deep infections, pulmonary complications, and gastrointestinal obstruction; reoperation during the postoperative period is sometimes necessary to address these complications. Rates of reoperation or conversion surgery beyond the postoperative period depend on the type of bariatric procedure, and in one study ranged from 17% to 31 %. Intestinal absorptive abnormalities, such as micronutrient deficiency and protein-calorie malnutrition, also are typically seen with bypass procedures, requiring lifelong nutrient supplementation. Major and serious adverse outcomes associated with bariatric surgery are common, observed in approximately 4 percent of procedures performed (including death in 0.3 to 2 percent of all patients receiving laparoscopic banding or bypass surgeries, respectively).

MetAP2 encodes a protein that functions at least in part by enzigmatically removing the amino terminal methionine residue from certain newly translated proteins such as glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al.(2003) Cancer Res. 63:7861) and infectious diseases such as microsporidiosis, leishmaniasis, and malaria (Zhang et al. (2002) *J. Biomed. Sci.* 9:34). However, such MetAP2 inhibitors may be useful as well for subjects with excess adiposity and conditions related to adiposity including type 2 diabetes, hepatic steatosis, and cardiovascular disease (via e.g. ameliorating insulin resistance, reducing hepatic lipid content, and reducing cardiac workload). Methods of treating obese subjects that are mote effective than e.g. dieting alone are clearly needed.

SUMMARY

The disclosure generally relates, at least in part, to methods for treating a subject having an overweight or obese condition or a related condition with pharmaceutical compositions including a MetAP-2 inhibitory compound, or a salt or ester thereof. In one aspect, the disclosure relates to methods of treating a subject having an overweight or obese condition including administering to the subject a therapeutically effective amount of a pharmaceutical composition as disclosed herein, for example, a compound of Formula I, II, III, IV, V, VI, VII, VIII, IX, X, XI, XII, XIII, XIV, XV, A-B, or C-D, and/or other compounds as disclosed herein. In one embodiment, the subject has a Body Mass Index measurement of at least about 25 kg/m$^2$, at least about 30 kg/m$^2$, or at least about 40 kg/m$^2$.

In certain embodiments the pharmaceutical composition is administered non-parenterally, for example, orally, buccally, sublingually, transdermally, via inhalation, or rectally. In other embodiments, the pharmaceutical composition is administered parenterally, for example, subcutaneously.

In one embodiment, administration results in decreased body fat and a substantial maintenance of muscle mass in the subject. In another embodiment, upon administration, fat oxidation is enhanced as compared to a subject on a restricted food intake diet alone. In another embodiment, substantially no loss of new blood vessels in the deposits occur as compared to a subject being treated for obesity using an energy restricted diet alone.

In one aspect, a disclosed method relates to controlling or preventing hepatic steatosis in an obese subject being treated for obesity, comprising administering a therapeutically effective amount of a pharmaceutical composition including a compound disclosed herein. Also provided herein is a method relating to improving liver function in an obese subject, including administering a therapeutically effective amount of a pharmaceutical composition including a compound described herein to the subject.

In another aspect, a disclosed method relates to improving exercise capacity in a subject in need thereof comprising administering a therapeutically effective amount of a pharmaceutical composition including a compound described herein to the subject.

A method relating to reducing weight of a subject in a subject in need thereof is also contemplated herein, including administering a therapeutically effective amount of a pharmaceutical composition including a compound described herein to the subject. For example, the metabolic rate of the subject may not substantially reduced as compared to the metabolic rate of a subject on an energy restricted diet alone. In another aspect, a disclosed method relates to restoring normal metabolic action in an obese subject in need thereof, including administering a therapeutically effective amount of a pharmaceutical composition including a compound disclosed herein to the subject.

Also provided herein is a method relating to decreasing body fat in an overweight or obese subject in need thereof, comprising administering a therapeutically effective amount of a pharmaceutical composition comprising a compound disclosed herein to the subject resulting in body fat reduction and substantial maintenance of muscle mass during the body fat reduction. In one embodiment, the subject retains substantially more muscle mass as compared to body fat reduction in a subject using an energy restricted diet alone.

In another aspect, a disclosed method relates to activating brown fat function and/or increasing brown fat tissue mass in a subject in need thereof, including administering a therapeutically effective amount of a pharmaceutical composition, including a compound disclosed herein to the subject.

In another aspect, a disclosed method relates to restoring and/or maintaining thyroid hormone concentrations in an obese subject, including administering a therapeutically effective amount of a pharmaceutical composition including a compound described herein to the subject.

In an exemplary embodiment, disclosed methods such as a method relating to treating a subject having an overweight or obese condition, includes administering to the subject a therapeutically effective amount of a pharmaceutical composition comprising the compound

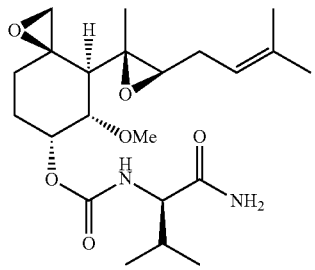

BRIEF DESCRIPTION OF THE DRAWINGS

The FIGURE is a graph showing effect of 7 days of administration of select disclosed compounds on body weight in DIO mice. Data is expressed as average weight of mice in grams.

DETAILED DESCRIPTION

Overview

The disclosure is directed in part to methods of reducing adipose tissue in an overweight subject using compounds that modulate MetAP-2. A MetAP-2 inhibitory compound is able to inhibit the activity of methionine aminopeptidase 2 (MetAP-2), e.g., the ability of MetAP-2 to cleave the N-terminal methionine residue of newly synthesized proteins to produce the active form of the protein. Exemplary MetAP-2 inhibitors are provided herein.

Obesity and being overweight refer to an excess of fat in proportion to lean body mass. Excess fat accumulation is associated with increase in size (hypertrophy) as well as number (hyperplasia) of adipose tissue cells. Obesity is variously measured in terms of absolute weight, weight: height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using the formulas: SI units: $BMI=weight(kg)/height^2(m^2)$, or US units: $BMI=(weight(lb)*703/(height^2 (in^2))$.

In accordance with the U.S. Centers for Disease Control and Prevention (CDC), an overweight adult has a BMI of 25 $kg/m^2$ to 29.9 $kg/m^2$, and an obese adult has a BMI of 30 $kg/m^2$ or greater. A BMI of 40 $kg/m^2$ or greater is indicative of morbid obesity or extreme obesity. For children, the definitions of overweight and obese take into account age and gender effects on body fat.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Another method is fan-beam dual energy X-ray absorptiometry (DEXA), DEXA allows body composition, particularly total body fat and/or regional fat mass, to be determined non-invasively.

Without being limited by any particular theory of mechanism of action, it is believed that fat oxidation and lipolysis are stimulated through treatment with inhibitors of MetAP2 that enhance the level and function of thioredoxin and/or over-rides the inhibitory effects of hyperinsulinemia related at least in part to insulin-stimulation and/or over-rides the inhibitory effects of high fat diet induced NADPH oxidase activity. A coordinated action can be induced which leads to a physiological reduction in body adiposity through increased loss of fat tissue-associated triglyceride, enhanced local generation of 3,5,3'-triiodothyronine active thyroid hormone with corresponding enhanced activity of brown adipose tissue and its sensitivity to physiological stimuli, increased metabolism of free fatty acids by the liver with increased ketone body formation, and reduced food intake. These effects are evident at doses of a MetAP2 inhibitor that do not substantially modulate angiogenesis.

In obese and/or hyperinsulinemic subjects, liver PKA functions may be suppressed secondary to elevated NADPH oxidase expression. Ketone body production and utilization are typically suppressed in an obese subject, potentially reducing hepatic satiety signals and increasing food consumption. However, administration of a MetAP2 inhibitor, without being limited by an theory, leads to inhibition of thioredoxin amino-terminal methionine processing and increases steady-state thioredoxin levels, reactivating protein kinase A (PKA) function, reactivating adipose tissue lipase activity and/or stimulating production and/or activity of the rate-limiting enzyme of beta-hydroxybutyrate production (3-hydroxymethyl glutaryl CoA synthase), leading to elevated ketone body production.

The coordinated and physiologic induction of anti-obesity activities mediated by the methods disclosed herein may lead to a healthy reduction in tissue levels of triglyceride, diacylglycerol, and other fat related mediators and oxidants, and can result in a new steady state situation that favors lean body composition and increased whole body energy metabolism. Without being bound by any theory, it is believed that the mechanistic cascade activated by MetAP2 inhibitors leads to fat tissue being converted to ketone bodies and burned as fuel, unlike existing therapies (including e.g., calorie or energy restricted diets) that target central control of food intake and that may carry adverse side effects (e.g. adverse neurological side effects). Further, therapeutically effective doses contemplated herein will not typically induce any anti-angiogenic action.

An effective therapy for treating a subject having an overweight or obese condition may reduce adipose tissue without resulting in deleterious side effects, for example, wasting. Wasting is characterized by degradation and loss of a substantial amount of lean body mass (muscle tissue, bones, and organs) in addition to adipose tissue. In particular, lean body mass refers to structural and functional elements in cells, body water, muscle, bones, and other body organs such as the heart, liver, and kidneys. Although weight loss may involve loss of fat along with slight loss of muscle or fluid, weight loss for the purposes of maintaining health should aim to lose fat while conserving lean body mass. Wasting involves uncontrollable weight loss.

Treatment induced wasting may occur as a side-effect of some drugs. High-dose sulphonamides, anti-mycobacterial agents, and other medications have been associated with anorexia and subsequent wasting. Substantial loss of lean body mass can lead to various diseases. Schaafsma (Current Topics in Nutriceutical Research (2006) ISSN 1540-7533 4 (2): 113-121). Health problems associated with loss of lean body mass include difficulty fighting off infection, osteoporosis, decreased muscle strength, trouble regulating body temperature, and even increased risk of death.

MetAP-2 Compounds

Compounds for use with the methods disclosed herein, include compounds of Formula I:

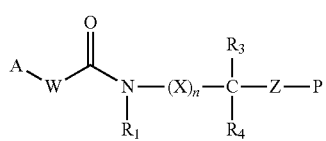

in which: A is a Met-AP2 inhibitory core; W is O or $NR_2$, $R_1$ and $R_2$ are each, independently, hydrogen or alkyl; X is alkylene or substituted alkylene; n is 0 or 1; $R_3$ and $R_4$ are each, independently, hydrogen, substituted or unsubstituted alkyl, substituted or unsubstituted aryl or substituted or unsubstituted heteroaryl; or $R_3$ and $R_4$, together with the carbon atom to which they are attached from a carbocyclic or heterocyclic group; or $R_3$ and $R_4$ together form an alkylene group; Z is —C(O)— alkylene of alkylene —C(O)—; and P is a peptide comprising from 1 to about 100 amino acid residues attached at its amino terminus to Z or a group $OR_5$ or $N(R_6)R_7$, in which $R_5$, $R_6$ and $R_7$ are each, independently, hydrogen, alkyl, substituted alkyl, azacycloalkyl or substituted azacycloalkyl; or $R_6$ and $R_7$, together with the nitrogen atom to which they are attached, from a substituted or unsubstituted heterocyclic ring structure; or Z is —O—, —$NR_8$—, alkylene-O— or alkylene-$NR_8$—, where $R_8$ is hydrogen or alkyl; and P is hydrogen, alkyl or a peptide consisting of from 1 to about 100 amino acid residues attached at its carboxy terminus to Z; in which the N-terminus of the peptide is —$NR_2R_3$, wherein $R_2$ is hydrogen, alkyl or arylalkyl and $R_3$, is hydrogen, alkyl, arylalkyl of acyl.

Exemplary compounds of Formula I include:

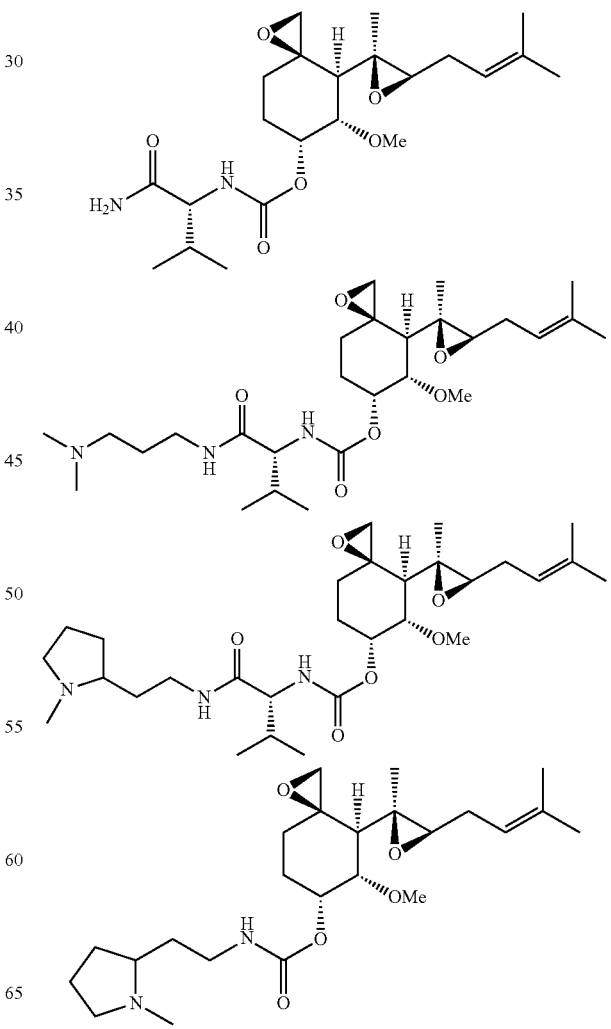

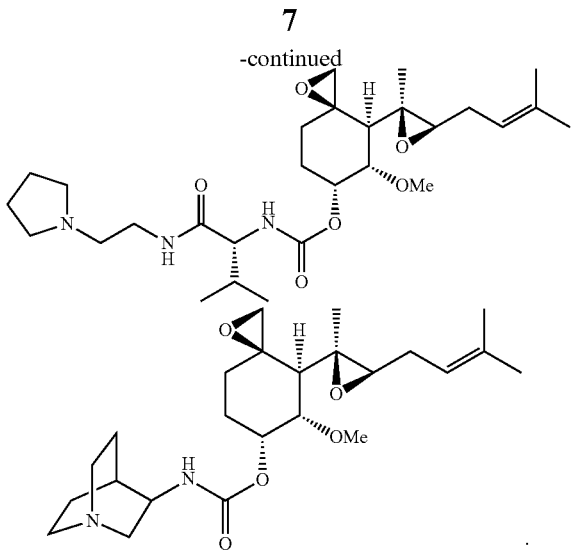

Further definitions and examples of substituents for each moiety in Formula I are shown in Olson et al. (U.S. Pat. No. 7,084,108 and WO 2002/042295). Further embodiments and examples of the compounds of Formula 1 are shown in Olson et al. (U.S. Pat. No. 7,084,108 and WO 2002/042295). Methods of making compounds of Formula I are shown in Olson et al. (U.S. Pat. No. 7,084,108 and WO 2002/042295).

In other embodiments, compounds for use with the methods disclosed herein include compounds of Formula II:

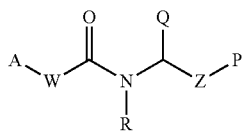

in which: A is a MetAP-2 inhibitory core; W is O or NR; each R is, independently, hydrogen or alkyl; Z is —C(O)— or -alkylene-C(O)—; P is NHR, OR or a peptide consisting of one to about one hundred amino acid residues connected at the N-terminus to Z; Q is hydrogen, a linear, branched or cyclic alkyl or aryl, provided that when. P is —OR, Q is not hydrogen; or Z is -alkylene-O— or -alkylene-N(R)—; P is hydrogen or a peptide consisting of from one to about one hundred amino acid residues connected to Z at the carboxyl terminus; Q is hydrogen or a linear, branched or cyclic alkyl or aryl, provided that when P is hydrogen, Q is not hydrogen; and pharmaceutically acceptable salts thereof. In a related embodiment, when P is a peptide, the N-terminus of the peptide is —NR$_2$R$_3$, wherein R$_2$ is alkyl or arylalkyl and R$_3$ is hydrogen, alkyl, arylalkyl, or acyl.

Further definitions and examples of substituents for each moiety in Formula II are shown in Olson et al. (U.S. Pat. Nos. 6,548,477; 7,037,890; 7,084,108; 7,268,111; and WO 2002/042295). Further embodiments and examples of the compounds of Formula II are shown in Olson et al. (U.S. Pat. Nos. 6,548,477; 7,037,890; 7,084,108; 7,268,111; and WO 2002/042295). Methods of making compounds of Formula II are shown in Olson et al. (U.S. Pat. Nos. 6,548,477; 7,037,890; 7,084,108; 7,268,111; and WO 2002/042295).

In other embodiments, compounds for use with the methods disclosed herein include compounds of Formula III:

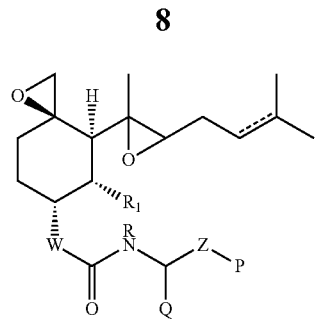

in which: W is O or NR; each R is, independently hydrogen or a C$_1$-C$_4$-alkyl; Q is hydrogen, a linear, branched or cyclic C$_1$-C$_6$-alkyl; or aryl; R$_1$ is hydroxy, C$_1$-C$_4$-alkoxy or halogen; Z is —C(O)— or C$_1$-C$_4$-alkylene-C(O)—; P is NHR, OR, or a peptide comprising 1 to 100 amino acid residues attached to Z at the N-terminus; or Z is alkylene-O or alkylene-NR; and P is hydrogen, or peptide comprising 1 to 100 amino acid residues attached to Z at the C-terminus; or a pharmaceutically acceptable salt thereof. In related embodiments, when P is a peptide, the N-terminus of the peptide is —NR$_2$R$_3$, wherein R$_2$ is alkyl or arylalkyl and R$_3$ is hydrogen, alkyl, arylalkyl, or acyl.

Further definitions and examples of substituents for each moiety in Formula III are shown in Olson et al. (U.S. Pat. Nos. 6,548,477; 7,037,890; 7,084,108; 7,268,111; and WO 2002/042295). Further embodiments and examples of the compounds of Formula III are shown in Olson et al. (U.S. Pat. Nos. 6,548,477; 7,037,890; 7,084,108; 7,268,111; and WO 2002/042295). Methods of making compounds of Formula III are shown in Olson et al. (U.S. Pat. Nos. 6,548,477; 7,037,890; 7,084,108; 7,268,111; and WO 2002/042295).

In other embodiments, the compounds for use with the methods disclosed herein include compounds of Formula A-B in which: A is a moiety selected from the group consisting of:

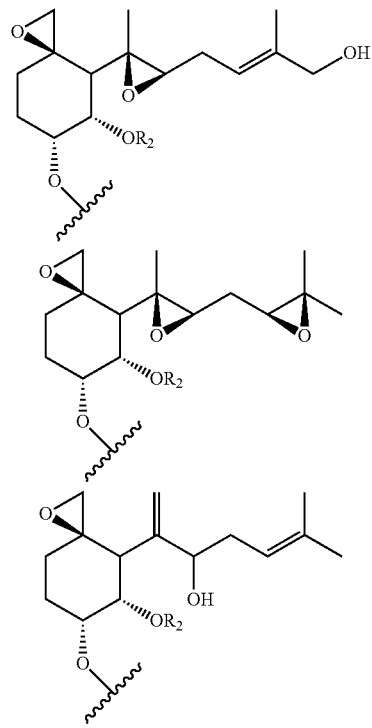

-continued

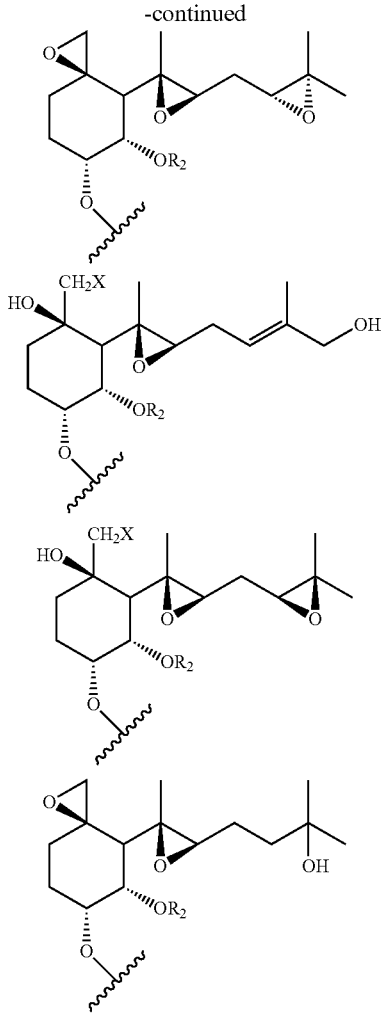

in which $R_2$ is hydrogen or $C_1$-$C_6$-alkyl and X is halogen, dialkylsulfinium, thioalkoxy or thioaryloxy; and B is an alkanoyl, aroyl, carbamoyl or substituted carbamoyl group; or a pharmaceutically acceptable salt thereof.

In related embodiments, B is a moiety of the formula:

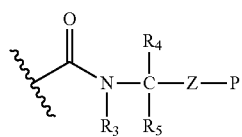

in which: $R_3$ is hydrogen or alkyl; $R_4$ and $R_5$ are each, independently, hydrogen, substituted or unsubstituted alkyl, substituted or unsubstituted aryl, substituted or unsubstituted arylalkyl, substituted or unsubstituted heteroaryl or substituted or unsubstituted heteroalkyl; or $R_3$ and $R_5$ together form an alkylene group; Z is —C(O)— or -alkylene-C(O)—; and P is —$OR_6$ or —N($R_7$)$R_8$, wherein $R_6$, $R_7$ and $R_8$ are each, independently, hydrogen, substituted or unsubstituted alkyl, substituted or unsubstituted aryl or substituted or unsubstituted azacycloalkyl or $R_7$ and $R_8$, together with the nitrogen atom to which they are attached, form a heterocyclic ring structure.

In related embodiments, B is a moiety of the formula:

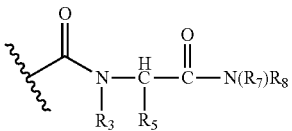

in which $R_5$ is substituted or unsubstituted linear, branched or cyclic $C_1$-$C_6$-alkyl, aryl, arylalkyl or heteroaryl; or $R_3$ and $R_5$ together form a $C_3$-$C_6$-alkylene group.

Further definitions and examples of substituents for each moiety in Formula A-B are shown in Olson et al. (WO 2005/066197). Further embodiments and examples of the compounds of Formula A-B are shown in Olson et al. (WO 2005/066197). Methods of making compounds of Formula A-B are shown in Olson et al. (WO 2005/066197).

In other embodiments, the compounds for use with the methods disclosed herein include compounds of Formula C-D in which: G is a moiety of the formula:

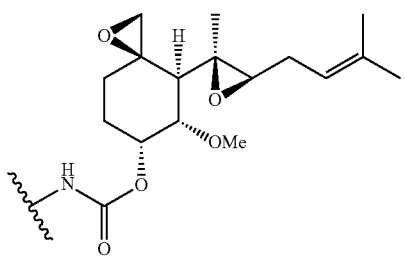

and D is a moiety of the formula:

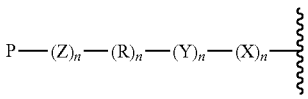

in which: n is independently an integer from 0-1; X is a linear or branched $C_1$-$C_6$-alkyl; Y is —C(O)—; R is NH; Z is a $C_1$-$C_6$-alkyl; and P is $NH_2$ or a moiety of the formula:

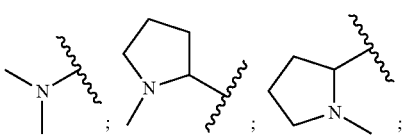

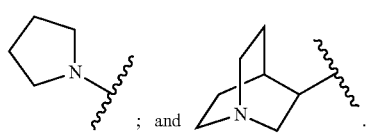

Exemplary compounds of Formula C-D include:

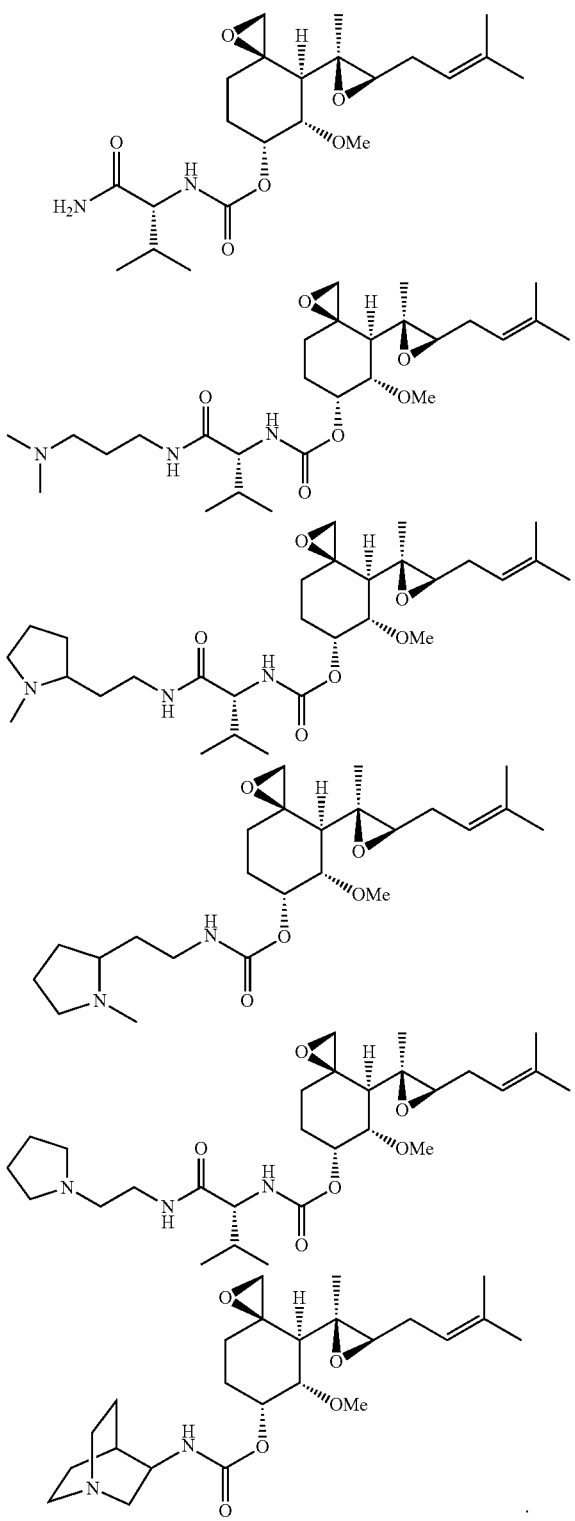

Further definitions and examples of substituents for each moiety in Formula C-D are shown in Olson et al. (U.S. Pat. No. 7,084,108 and WO 2002/042295). Further embodiments and examples of the compounds of Formula C-D are shown in Olson et al. (U.S. Pat. No. 7,084,108 and WO 2002/

04225). Methods of making compounds of Formula C-D are shown in Olson et al. (U.S. Pat. No. 7,084,108 and WO 2002/042295).

Methods disclosed here include administering a pharmaceutical composition including disclosed compounds that may result in the desirable effect of a reduction in adipose tissue but without resulting in deleterious side effects, for example, wasting. In certain embodiments, the compounds are compounds of Formula IV:

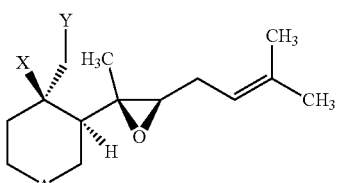

(IV)

or a pharmaceutically acceptable salt, ester, or prodrug thereof, wherein a) —X is —OH; and —Y is chosen from halogen and,

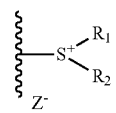

wherein $R_1$ and $R_2$ are individually chosen from —H and substituted or unsubstituted lower alkyl, with the proviso that $R_1$ and $R_2$ are not both —H; and Z is a counter ion; or —X and —Y taken together form an oxirane ring; and b) -A- is chosen from

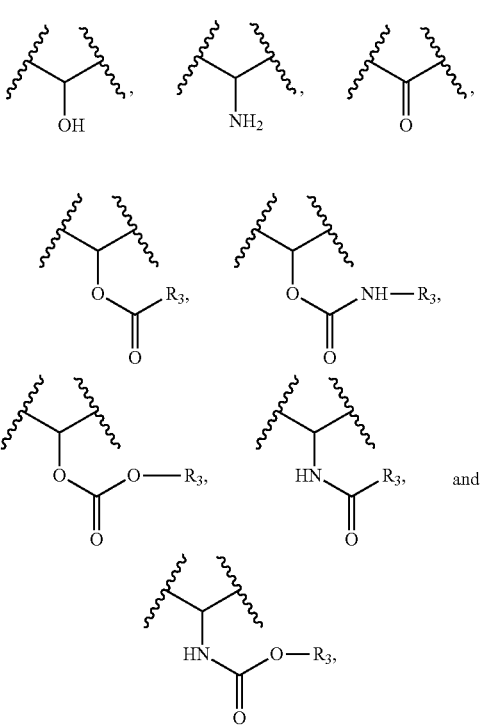

and wherein R₃ is chosen from substituted or unsubstituted lower alkyl substituted or unsubstituted alkanoyl, substituted or unsubstituted aryl, substituted or unsubstituted arylalkyl and arylalkanoyl.

Further definitions and examples of substituents for each moiety in Formula IV are shown in Hong et al. (U.S. Pat. No. 6,040,337). Further embodiments and examples of the compounds of Formula IV are shown in Hong et al. (U.S. Pat. No. 6,040,337). Methods of making compounds of Formula IV are shown in Hong et al. (U.S. Pat. No. 6,040,337).

In other embodiments, the compounds for use with the methods disclosed herein include compounds of Formula V:

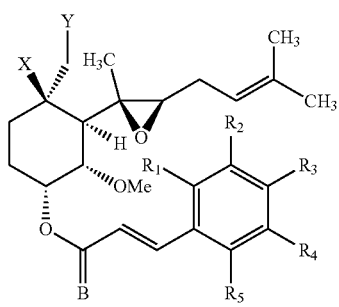

(V)

of a pharmaceutically acceptable salt, ester, or prodrug thereof,
wherein: a) X is —OH and Y is halogen or X and Y taken together form an oxirane ring; b) B is selected from O and H₂; and c) $R_1$, $R_2$, $R_3$, $R_4$ and $R_5$ are independently chosen from —H, —OH, acetoxy, substituted or unsubstituted amino, substituted or unsubstituted alkyl, substituted or unsubstituted aminoalkoxy, $C_1$-$C_6$ alkoxy, halogen, cyano, trifluoromethyl, nitro, alkylenedioxy, formyl, acetamido and methylenoxycarboxy, with the proviso that $R_1$, $R_2$, $R_3$, $R_4$ and $R_5$ are not each —H. In a related embodiment, $R_1$, $R_2$, $R_3$, $R_4$ and $R_5$ are independently chosen from —H, —OH, acetoxy, amino, alkylamino, dialkylamino, dialkylaminoalkyl, akylaminoalkoxy, dialkylaminoalkoxy, $C_1$-$C_6$ alkoxy, halogen, cyano, trifluoromethyl, nitro, and methylenedioxy.

Further definitions and examples of substituents for each moiety in Formula V are shown in Hong et al. (U.S. Pat. No. 6,063,812 and WO 1999/059986). Further embodiments and examples of the compounds of Formula V are shown in Hong et al. (U.S. Pat. No. 6,063,812 and WO 1999/059986). Methods of making compounds of Formula V are shown in Hong et al. (U.S. Pat. No. 6,063,812 and WO 1999/059986).

In other embodiments, the compounds for use with the methods disclosed herein include compounds of Formula VI:

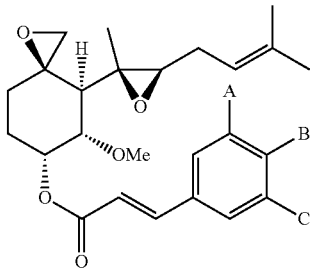

(VI)

or a pharmaceutically acceptable salt, ester, or prodrug thereof, wherein A, B and C represent independently or simultaneously hydrogen, $C_1$-$C_6$ alkoxy, halogen, $C_1$-$C_6$ alkyl, trifluoromethyl, cyano, nitro, 4-hydroxymethylphenoxy, —X—$(CH_2)_n$-OH or —X—$(CH_2CH_2O)_m$-$CH_2CH_2OH$, wherein X represents nitrogen or oxygen; n is 3, 4, 5 or 6; and m is 0, 1 or 2, with proviso that at least one of above A, B, C is one substituent selected from 4-hydroxymethylphenoxy, —X—$(CH_2)_n$—OH or —X—$(CH_2CH_2O)_m$-$CH_2CH_2OH$.

Further definitions and examples of substituents for each moiety in Formula VI are shown in Lee et al. (WO 2006/080591), Further embodiments and examples of the compounds of Formula VI am shown in Lee et al. (WO 2006/080591), Methods of making compounds of Formula VI are shown in Lee et al. (WO 2006/080591).

In certain embodiments, the contemplated compounds, include those of Formula VII:

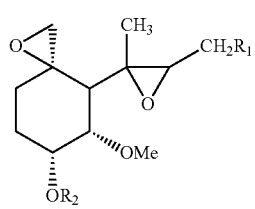

(VII)

wherein: $R_1$ is a 2-methyl-1-propenyl or isobutyl group which may be substituted by hydroxyl or di-$C_{1-3}$alkylamino; and $R_2$ is (1) carbamoyl which may optionally be substituted by (i) $C_{1-6}$alkyl which may be substituted by halogen, di-$C_{1-3}$alkylamino, nitro, $C_{1-6}$alkyloxycarbonyl or trimethylammonio halide, (ii) $C_{1-6}$alkylthio, $C_{1-6}$alkanoylthio, (iii) acryloyl or methacrylolyl, (iv) phenyl, naphthyl, benzoyl or benzenesulfonyl which may be substituted by halogen, trifluoromethyl, chloromethyl, naphthyl, benzoyl, $C_{1-6}$alkyl, $C_{1-6}$alkoxy, di-$C_{1-3}$alkylamino, nitro, $C_{1-6}$alkanolyloxy or $C_{1-6}$alkanoylthio on the ring, (v) $C_{1-6}$alkoxycarbonyl, $C_{1-6}$alkoxycarbonylmethyl, or carboxymethyl, (vi) phenoxycarbonyl which may be substituted by halogen or $C_{1-6}$-alkanoyl, naphthyl or benzoyl, or (ix) chloroacetyl; (2) benzenesulfonyl which may be substituted by $C_{1-6}$alkyl or halogen; (3) $C_{1-6}$alkylsulfonyl; or (4) sulfamoyl which may be substituted by $C_{1-6}$alkyl or phenyl; or a pharmaceutically acceptable salt, ester, or prodrug thereof.

Other contemplated compounds include O-chloroacetylcarbamoylfumigillol, O-chloroacetylcarbamoyldihydrofumagillol, or O-chloroacetylcarbamoyl-6b-hydroxyfumagillol.

Further definitions and examples of substituents for each moiety in formula VII are shown in Kishimoto et al. (U.S. Pat. No. 5,166,172; 5,698,586; 5,164,410; and 5,180,738). Further embodiments and examples of the compounds of Formula VII are shown in Kishimoto et al. (U.S. Pat. Nos. 5,166,172; 5,698,586; 5,164,410; and 5,180,738). Methods of making compounds of formula VII are shown in Kishimoto et al. (U.S. Pat. Nos. 5,166,72; 5,698,586; 5,464, 410; and 5,180,738), In other embodiments, the compounds are compounds of Formula VIII:

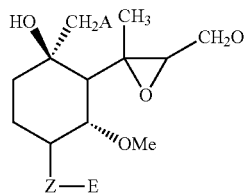

(VIII)

wherein A is halogen, —N(O)mR$_1$R$_2$—N$^+$ R$_1$R$_2$R$_3$X$^-$, —S(O)nR$_1$ or S$^+$(O)mR$_1$R$_2$Xβ; and in which R$_1$, R$_2$ and R$_3$ independently are: (1) a C$_{1-6}$alkyl, C$_{2-6}$alkenyl, C$_{2-6}$alkynyl, C$_{3-6}$cycloalkyl, C$_{3-6}$cycloalkenyl, C$_{7-13}$aralkyl or C$_{6-10}$aryl group, each of which is unsubstituted or substituted by (i) C$_{1-6}$alkyl, (ii) C$_{2-6}$alkenyl, (iii) C$_{3-6}$alkynyl, (iv) C$_{1-6}$cycloalkyl, (v) C$_{3-6}$cycloalkenyl, (vi) C$_{6-10}$aryl, (vii) hydroxyl, (xiv) C$_{1-4}$alkoxy, (xv) C$_{6-10}$aryloxy, (xvi) C$_{1-6}$alkylthio, (xvii) C$_{6-10}$arylthio, (xviii) cyano, (xix) carbamoyl, (xx) carboxyl, (xxi) C$_{1-4}$alkoxy-carbonyl, (xxii) C$_{7-11}$aryloxycarbonyl, (xxiii) carboxy-C$_{1-4}$alkoxy, (xxiv) C$_{1-6}$alkanoyl, (xxv) C$_{7-11}$aroyl, (xxvi) C$_{6-10}$arylsulfonyl, (xxvii) C$_{1-6}$alkylsulfinyl, (xxviii) C$_{6-10}$arylsulfinyl, (xxix) C$_{1-6}$alkylsufonyl, (xxx) a 5- or 6-membered heterocyclic group containing 1 to 4 hetero atoms of nitrogen, oxygen and/or sulfur, (xxxi) a 5- or 6-membered heterocyclic-carbonyl group containing 1 to 4 hetero atoms of nitrogen, oxygen and/or sulfur, or (xxxii) a 5- or 6-membered heterocyclic-thio group containing 1 to 4 hetero atoms of nitrogen, oxygen and/or sulfur which may be fused with a benzene ring, wherein groups (i) to (xxxii) are unsubstituted or further substituted by one to three groups or any of groups (i) to (xxxii) as defined above, or (2) a 5- or 6-membered heterocyclic group containing 1 to 4 hetero atoms of nitrogen, oxygen and/or sulfur, which is unsubstituted or substituted by the substituent(s) on the C$_{1-6}$alkyl, C$_{2-6}$alkenyl, C$_{2-6}$alkynyl, C$_{3-6}$cycloalkyl, C$_{3-6}$cycloalkenyl, C$_{7-13}$aralkyl or C$_{6-10}$aryl group as defined in (1) of R$_1$, R$_2$ and R$_3$ and which may be fused with benzene, pyridine or cyclohexane; X$^+$ is a counter anion; m is an integer of 0 or 1; n is an integer of 0 to 2; R$_1$, and R$_2$ together with an adjacent nitrogen atom may form a 4 to 7 membered nitrogen-containing heterocyclic group which is unsubstituted or substituted by the substituent(s) on the C$_{1-6}$alkyl, C$_{2-6}$alkenyl, C$_{2-6}$alkynyl, C$_{3-6}$cycloalkyl, C$_{3-6}$cycloalkenyl, C$_{7-13}$aralkyl or C$_{6-10}$aryl groups as defined in (1) of R$_1$, R$_2$ and R$_3$, and which may be fused with benzene, pyridine, pyrazine, pyridazine, cyclohexane or cyclohexene, or R$_1$ and R$_2$ together with an adjacent sulfur atom may form a 4 to 7 membered sulfur-containing heterocyclic group which is unsubstituted or substituted by the substituent(s) on the C$_{1-6}$alkyl, C$_{2-6}$alkenyl, C$_{2-6}$alkynyl, C$_{3-6}$cycloalkyl, C$_{3-6}$cycloalkenyl, C$_{7-13}$aralkyl or C$_{6-10}$aryl groups as defined in (1) of R$_1$, R$_2$ and R$_3$, and which may be fused with benzene, pyridine, pyrazine, pyridazine, cyclohexane or cyclohexene; Z is —NR$_4$ wherein R$_4$ is hydrogen, or C$_{1-6}$alkyl, C$_{6-10}$aryl group, each of which is unsubstituted or substituted by the substituent(s) on the C$_{1-6}$alkyl, C$_{2-6}$alkenyl, C$_{3-6}$alkynyl, C$_{3-6}$cycloalkyl, C$_{3-6}$cycloalkenyl, C$_{7-13}$aralkyl or C$_{6-10}$aryl groups as defined in (1) of R$_1$, R$_2$ and R$_3$; D is 2-methyl-1-propenyl or isobutyl; E is (i) hydrogen, (ii) a group as defined in (1) of R$_1$, R$_2$ and R$_3$, or (iii) a C$_{1-10}$alkanoyl, C$_{7-11}$aroyl, 5- or 6-membered heterocyclic carbonyl containing 1 to 4 hetero atoms of nitrogen, oxygen and/or sulfur, carbamoyl, thiocarbamoyl, C$_{6-10}$arylsulfonyl, C$_{1-6}$alkylsulfonyl, sulfamoyl, C$_{2-7}$alkoxycarbonyl or C$_{7-11}$aryloxycarbonyl group which is unsubstituted or substituted by the substituent(s) on the C$_{1-6}$alkyl, C$_{2-6}$alkenyl, C$_{2-6}$alkynyl, C$_{3-6}$cycloalkyl, C$_{3-6}$cycloalkenyl, C$_{7-13}$aralkyl or C$_{6-10}$aryl groups as defined in (1) of R$_1$, R$_2$ and R$_3$, provided that, when A is chlorine, E is a group of (ii), or group of (iii) excepting dinitrobenzoyl; or a pharmaceutically acceptable, salt, ester, or prodrug thereof.

Further definitions and examples of substituents for each moiety in Formula VIII are shown in Kishimoto et al. (U.S. Pat. No. 5,180,735). Further embodiments and examples of the compounds of Formula VIII are shown in Kishimoto et al. (U.S. Pat. No. 5,180,735). Methods of making compounds of Formula VIII are shown in Kishimoto et al. (U.S. Pat. No. 5,180,735).

In other embodiments, the compounds are compounds of Formula IX:

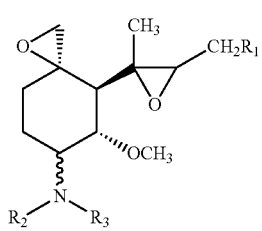

(IX)

wherein: R$_1$ is a 2-methyl-1-propenyl or isobutyl; R$_2$ is (1) hydrogen atom, (2) a C$_{1-20}$alkyl group which may be substituted with amino, C$_{1-6}$alkylamino; di-C$_{1-6}$alkylamino, nitro, halogen, hydroxyl, C$_{1-6}$alkoxy, phenyl which may be substituted by C$_{1-6}$alkyl, C$_{1-6}$alkoxy, halogen, halogenated alkyl or nitro, or (3) a C$_{6-12}$aryl group which may be substituted with C$_{2-6}$alkyl, (ii) amino halogen, hydroxyl, C$_{1-6}$alkoxy, cyano, carbamoyl or carboxyl; R$_3$ is: (1) hydrogen atom, (2) a C$_{1-20}$alkyl group which may be substituted with amino, C$_{1-6}$alkylamino, di-C$_{1-6}$alkylamino, nitro, halogen, hydroxyl, C$_{1-6}$alkylthio, C$_{1-6}$alkoxy, cyano, carbamoyl, carboxyl, C$_{1-6}$alkoxycarbonyl, carboxy-C$_{1-6}$alkoxy, phenyl which may be substituted by C$_{1-6}$alkyl, C$_{1-6}$alkoxy, halogen, halogenated alkyl or nitro, or a 5- or 6-membered aromatic heterocyclic group containing 1 to 4 hetero atoms selected from nitrogen, oxygen and sulfur, and said alkyl group may be epoxidated at an optional position, (3) a C$_{1-20}$alkanoyl group which may be substituted with amino, C$_{1-6}$alkylamino, di-C$_{1-6}$alkylamino, nitro, halogen, hydroxy, C$_{1-6}$alkylthio, C$_{1-6}$alkoxy, cyano, carbamoyl, carboxyl, C$_{1-6}$alkoxycarbonyl, carboxy-C$_{1-6}$alkoxy, phenyl which may be substituted by C$_{1-6}$alkyl, C$_{1-6}$alkoxy, halogen, halogenated alkyl or nitro, or a 5- or 6-membered aromatic heterocyclic group containing 1 to 4 hetero atoms selected from nitrogen, oxygen and sulfur, (4) a C$_{6-10}$aroyl group which may be substituted with C$_{3-6}$alkyl, amino, halogen, hydroxyl, (v) C$_{1-6}$alkyl, C$_{1-6}$alkanoyl, halogeno-C$_{1-6}$alkanoyl, C$_{1-6}$alkoxycarbonylmethyl, carboxymethyl, phenyl which may be substituted by C$_{1-6}$alkyl, C$_{1-6}$alkoxy, halogen, halogenated alkyl or nitro, naphthyl, benzoyl, naphthoyl or substituents forming cyclic amino group, taken together with the nitrogen atom of the carbamoyl group, (6) benzenesulfonyl group which may be substituted with C$_{1-6}$alkyl or halogen, (7) a C$_{1-6}$alkylsulfonyl group which may be substituted with the same substituent(s) as those of substituted C$_{2-20}$alkanoyl group mentioned in above (3), (8) thiocarbamoyl group which may be substituted with the same substituents(s) as those of a substituted carbamoyl group mentioned in above (5), (9) a $C_{1-6}$alkoxycarbonyl group which may be substituted with the same substituent(s) as those of a substituted $C_{2-20}$alkanoyl group mentioned in above (3), (10) phenoxycarbonyl group which may be substituted with the same substituent(s) as those of a substituted benzenesulfonyl group mentioned in above (6), or (11) a 5- or 6-membered aromatic heterocyclic carbonyl group containing 1 to 4 hetero atoms selected from nitrogen, oxygen and sulfur which may be substituted with the same substituent(s) as those of a substituted $C_{6-10}$aroyl group mentioned in above (4), wherein said aromatic heterocyclic carbonyl group is selected from the group consisting of 2-furoyl, 2-thenoyl, nicotinoyl and isonicotinoyl; $R_2$ and $R_3$ may form pyrolidine, piperidine or isoindoline ring which may be substituted with $C_{1-3}$alkyl or oxo; and the bonding mark ∿∿∿ represents an α-linkage or β-linkage; or a pharmaceutically acceptable salt, ester, or prodrug thereof.

Further definitions and examples of substituents for each moiety in Formula IX are shown in Kishimoto et al. (U.S. Pat. No. 5,288,722). Further embodiments and examples of the compounds of Formula IX are shown in Kishimoto et al. (U.S. Pat. No. 5,288,722). Methods of making compounds of Formula IX are shown in Kishimoto et al. (U.S. 5,288,722).

In other embodiments, the compounds are compounds of Formula X:

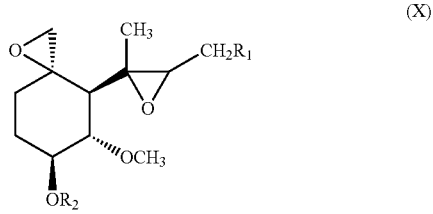

(X)

wherein: $R_1$ is 2-methyl-1-propenyl group or isobutyl group; $R_2$ is: (1) hydrogen atom; (2) a $C_{1-20}$alkanoyl which may be substituted with an amino, hydroxyl, halogen or carboxyl; (3) a benzoyl or naphthoyl which may be substituted with a $C_{2-6}$alkyl, amino, halogen, hydroxyl, C.sub.1-6 alkoxy, cyano, carbamoyl or carboxyl; (4) a 2-furoyl, 2-thienoyl, nicotinoyl, isonicotinoyl, or imidazole-1-carbonyl group which may be substituted with a $C_{2-6}$alkyl, amino, halogen, hydroxyl, $C_{1-6}$alkoxy, cyano, carbamoyl or carboxyl; (5) a carbamoyl which may be substituted with a $C_{1-6}$alkanoyl, chloroacetyl, dichloroacetyl, trichloroacetyl, $C_{1-6}$alkoxycarbonylmethyl, carboxymethyl, phenyl, naphthyl or benzoyl, or form a cyclic amino group together with the adjacent nitrogen atom selected from the group consisting of pyrrolidino, piperidino, morpholino, piperazino or 4-phenylpiperazino; (6) a $C_{1-6}$alkoxycarbonyl which may be substituted with an amino, hydroxyl, halogen or carboxyl; (7) a phenoxycarbonyl which may be substituted with a $C_{1-6}$alkyl or halogen; (8) a benzenesulfonyl which may be substituted with one to three substituents selected from a $C_{1-6}$alkyl and halogen; (9) a $C_{1-6}$alkylsulfonyl which may be substituted with an amino, hydroxyl, halogen or carboxyl; or (10) a sulfamoyl which may be substituted with a $C_{1-6}$alkyl or phenyl; or a pharmaceutically acceptable salt, ester, or prodrug thereof.

Further definitions and examples of substituents for each moiety in Formula X are shown in Kishimoto et al. (U.S. Pat. No. 5,704,345). Further embodiments and examples of the compounds of Formula X are shown in Kishimoto et al. (U.S. Pat. No. 5,204,345). Methods of making compounds of Formula X are shown in Kishimoto et al. (U.S. Pat. No. 5,204,345).

In other embodiments, the compounds are compounds of Formula XI:

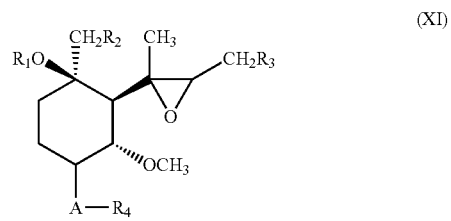

(XI)

wherein: $R_1$ is hydrogen; $R_2$ is halogen, $N(O)_m$ $R_5R_6$, $N^+R_5R_6R_7X^-$, $Si(O)_nR_5$ or $S^+$ $R_5$ $R_6X^-$, in which $R_5$, $R_6$ and $R_7$ represent each independently a substituted or unsubstituted hydrocarbon group or a substituted or unsubstituted heterocyclic group; $X^-$ represents a counter anion; m represents 0 or 1; n represents an integer of 0 to 2; or $R_5$ and $R_6$ together with the adjacent nitrogen or sulfur atom may form a nitrogen- or sulfur-containing heterocyclic group which is substituted or unsubstituted and may form a condensed ring; or $R_1$ and $R_2$ together are a chemical bond; $R_3$ is a substituted or unsubstituted 2-methyl-1-propenyl group or a substituted or unsubstituted isobutyl group; A is O or $NR_8$, in which $R_8$ represents hydrogen, a substituted or unsubstituted lower alkyl group or a substituted or unsubstituted aryl group; and $R_4$ is hydrogen, a substituted or unsubstituted hydrocarbon group or a substituted or unsubstituted acyl group; or a salt thereof, and a fatty acid ester of glycerin or polyglycerin wherein the fatty acid constituting the fatty acid ester is a saturated fatty acid having 6 to 22 carbon atoms.

Further definitions and examples of substituents for each moiety in Formula XI are shown in Kishimoto et al. (U.S. Pat. No. 5,422,363). Further embodiments and examples of the compounds of Formula XI are shown in Kishimoto et al. (U.S. Pat. No. 5,422,363). Methods of making compounds of Formula XI are shown in Kishimoto et al. (U.S. Pat. No. 5,422,363).

Methods disclosed herein include administering a pharmaceutical composition including MetAP-2 inhibitory compounds that result in the desirable effect of a reduction in adipose tissue but without resulting in deleterious side effects, for example, wasting. In certain embodiments, the compounds are compounds of Formula XII:

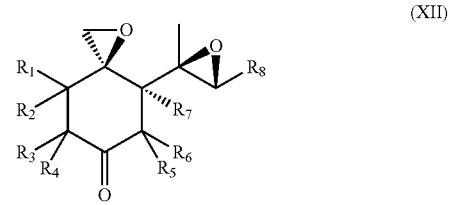

(XII)

or a pharmaceutically acceptable salt, ester, or prodrug thereof, wherein: $R_1$, $R_2$, $R_3$, $R_4$, $R_5$ and $R_6$ can be the same or different from each other, and are hydrogen alkyl aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether; $R_7$ is hydrogen or an hydroxy group; and $R_8$ (1) a substituted alkyl, allyl or alkyne group; or (2) a substituted alkoxyl or thioalkoxyl group, or methylene or ethylene alkoxyl or thioalkoxyl group, wherein the methylene or ethylene can be optionally substituted; or (3) an aroyl group which can be optionally substituted with at least one substituent selected from the group consisting of alkyl. amino, alkylamino, dialkylamino, halogen, hydroxyl, lower alkoxy, cyano, amido, carbamoyl, thiocarbamoyl, carbonyldioxyl , carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted, with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) an alkyl group which can be optionally substituted with $N^+P_1P_2P_3X^-$ or $S^+P_1P_2X^-$, wherein $P_1$, $P_2$ and $P_3$ can be the same or different and are each an optionally substituted hydrocarbon or heterocyclic group and $X^-$ is a counter anion; or (7) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (8) 2-methyl-1-propenyl or an isobutyl group which can be optionally substituted with $N^+P_1P_2P_3X^-$ or $S^+P_1P_2X^-$, wherein $P_1$, $P_2$ and $P_3$ can be the same or different and are each an optionally substituted hydrocarbon or heterocyclic group and X is a counter anion; or (9) a benzenesulfonyl, methylsulfonyl or alkyl sufonyl group, with or without a methylene or ethylene substituent, or the corresponding amide or ester, which can be optionally substituted; or (10) an alkoxycarbonyl or phenoxycarbonyl group with or without a methylene or ethylene substituent, which can be optionally substituted.

Further definitions and examples of substituents for each moiety in Formula XII are shown in Liu et al. (U.S. Pat. Nos. 6,207,704; 6,566,541; and WO 1998/056372). Further embodiments and examples of the compounds of Formula XII are shown in Liu et al. (U.S. Pat. Nos. 6,207,704; 6,566,541; and WO 1998/056372). Methods of making compounds of Formula XII as shown in Liu et al. (U.S. Pat. Nos. 6,207,704; 6,566,541; and WO 1998/056372).

In other embodiments, the compounds are compounds of Formula XIII:

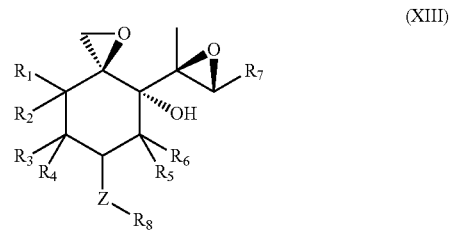

(XIII)

or a pharmaceutically acceptable salt, ester, or prodrug thereof, wherein: Z is an oxygen and can have R or S configuration; $R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted, aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether; $R_7$ and $R_9$ can be the same or different from each other and are: (1) hydrogen or a substituted alkyl, allyl or alkyne group; (2) a substituted alkoxyl or thioalkoxyl group, or methylene or ethylene alkoxyl or thioalkoxyl group, wherein the methylene or ethylene can be optionally substituted; or (3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) an alkyl group which can be optionally substituted with $N^+P_1P_2P_3X^-$ or $S^+P_1P_2X^-$, wherein $P_1$, $P_2$ and $P_3$ can be the same or different and are each an optionally substituted hydrocarbon or heterocyclic group and X is a counter anion; or (7) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (8) 2-methyl-1-propenyl or an isobutyl group which can be optionally substituted with $N^+P_1P_2P_3X^-$ or $S^+P_1P_2X^-$, wherein $P_1$, $P_2$ and $P_3$ can be the same or different and are each an optionally substituted, hydrocarbon or heterocyclic group and X is a counter anion; or (9) a benzenesulfonyl, methylsulfonyl or alkyl sulfonyl group, with or without a methylene or ethylene substituent, or the corresponding amide or ester, which can be optionally substituted; or (10) an alkoxycarbonyl or phenoxycarbonyl group with or without a methylene or ethylene substituent, which can be optionally substituted.

Further definitions and examples of substituents for each moiety in Formula XIII as shown in Liu et al. (U.S. Pat. Nos. 6,207,704; 6,566,541; and WO 1998/056372). Further embodiments and examples of the compounds of Formula XIII are shown in Liu et al. (U.S. Pat. Nos. 6,207,704; 6,566,541; and WO 1998/056372). Methods of making compounds of Formula XIII are shown in Liu et al. (U.S. Pat. Nos. 6,207,704; 6,566,541; and WO 1998/056372).

In other embodiments, the compounds are compounds of Formula XIV:

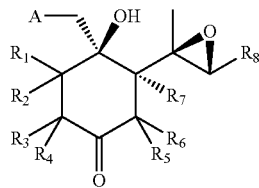

(XIV)

or a pharmaceutically acceptable salt, ester, or prodrug thereof, wherein: A is a halogen, $N^+P_1P_2P_3X^-$ or $S^+P_1P_2X^-$, wherein $P_1$, $P_2$ and $P_3$ can be the same or different and are each an optionally substituted hydrocarbon or heterocyclic group and X is a counter anion; $R_1$, $R_2$, $R_3$, $R_4$, $R_5$ and $R_6$ can be the same or different from each other, and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether; $R_7$ is hydrogen or an hydroxy group; and $R_8$ is (1) a substituted alkyl, allyl or alkyne group; or (2) a substituted alkoxyl or thioalkoxyl group, or methylene or ethylene alkoxyl or thioalkoxyl group, wherein the methylene or ethylene can be optionally substituted; or (3) an aroyl group which can be optionally substituted with at least one substituent selected from the group consisting of alkyl, amino, alkylamino, dialkylamino, halogen, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino. dialkylamino, halgen, hydroxyl, cyano, amido, carbamoyl, thiocarbamoyl, carbonyldioxyl, carboxyl, alkyl dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester or carboxyl salt; or (6) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (7) a benzenesulfonyl, methylsulfonyl or alkyl sufonyl group, with or without a methylene or ethylene substituent, or the corresponding amide or ester which can be optionally substituted; or (8) an alkoxycarbonyl or phenoxycarbonyl group with or without a methylene or ethylene substituent, which can be optionally substituted.

Further definitions and examples of substituents for each moiety in Formula XIV are shown in Liu et al. (U.S. Pat. Nos. 6,207,704; 6,566,541; and WO 1998/056372). Further embodiments and examples of the compounds of Formula XIV are shown in Liu et al, (U.S. Pat. Nos. 6,207,704; 6,566,541; and WO 1998/056372), Methods of making compounds of Formula XIV as shown in Liu et al. (U.S. Pat. Nos. 6,207,704; 6,566,541; and WO 1998/056372).

In other embodiments, the compounds are compounds of Formula XV:

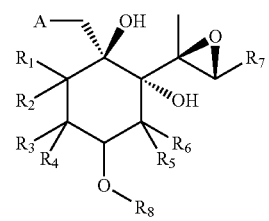

(XV)

or a pharmaceutically acceptable salt, ester, or prodrug thereof, wherein: A is a halogen, $N^+P_1P_2P_3X^-$ or $S^+P_1P_2X^-$, wherein $P_1$, $P_2$ and $P_3$ can be the same or different and are each an optionally substituted hydrocarbon or heterocyclic group and $X^-$ is a counter anion; $R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl of aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether; $R_7$ is hydrogen or an hydroxy group; and $R_8$ is: (1) hydrogen or a substituted alkyl, allyl or alkyne group; or (2) a substituted alkoxyl or thioalkoxyl group, or methylene of ethylene alkoxyl or thioalkoxyl group, wherein the methylene of ethylene can be optionally substituted; or (3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl cyclic or aromatic cyclic group which can be optionally substituted, or a heterocyclic or aromatic heterocyclic group which can be optionally substituted; of (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted a heterocyclic or aromatic heterocyclic group which can be optionally substituted, carboxylic acid, carboxyl ester, carboxyl salt; or (6) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (7) a benzenesulfonyl, methylsulfonyl or alkyl sufonyl group, with or without a methylene, or ethylene substituent, or the corresponding amide or ester, which can be optionally substituted; or (8) an alkoxycarbonyl or phenoxycarbonyl group with or without a methylene or ethylene substituent, which can be optionally substituted.

Further definitions and examples of substituents for each moiety in Formula XV are shown in Liu et al. (U.S. Pat. Nos. 6,207,704; 6,566,541; and WO 1998/056372). Further embodiments and examples of the compounds of Formula XV are shown in Liu et al. (U.S. Pat. Nos. 6,207,704; 6,566,541; and WO 1998/056372). Methods of making compounds of Formula IV are shown in Liu et al. (U.S. Pat. Nos. 6,207,704; 6,566,541; and WO 1998/056372).

Methods

A method of treating obesity in a subject in need thereof is provided herein, comprising parenterally or non-parenterally administering a therapeutically effective amount of a MetAP2 inhibitor, such as a disclosed compound to said subject. In some embodiments, a contemplated therapeutically effective amount of a disclosed compound as described below, does not substantially modulate or suppress angiogenesis but is still effective as MetAP2 inhibitor. The term angiogenesis is known to persons skilled in the art, and refers to the process of new blood vessel formation, and is essential for the exponential growth of solid tumors and tumor metastasis. For example, provided herein is a method of treating obesity in a subject in need thereof, comprising administering a therapeutically effective amount of a MetAP2 inhibitor, e.g., a disclosed compound to said subject, wherein substantially no loss of new blood vessels in fat deposits or other tissue compartments occur as compared to a subject being treated for obesity using an energy restricted diet alone.

For example, disclosed compounds may irreversibly inhibit enzymatic activity of MetAP2, leading to N-terminal acetylation and stabilization of these proteins at doses considerably lower than those required to suppress angiogenesis or tumor growth in vivo. Without being limited to any theory, the long-lasting covalent inhibition of MetAP2 enzymatic activity driven by such MetAP2 inhibitors may be responsible for the segregation of angiogenic effects from metabolic responses mediated by increased thioredoxin and/ or glyceraldehyde-3-phosphate levels in vivo. Alternatively, antitumor effects driven by angiogenesis inhibition may require a more thorough starvation of the tumor by heavily restricting blood supply, which requires high doses. Metabolic effects, however, may require a minor and incomplete perturbation of the system which occurs at lower doses and without any obvious direct effect on blood vessels.

Treated subjects used the disclosed methods may have a lower systemic exposure to said MetAP2 inhibitor as compared to a subject parenterally administered the same of amount of the MetAP2 inhibitor. In an exemplary embodiment, the disclosed methods may result in less accumulation in the reproductive tract (e.g. testis) of a subject, for example, as compared so the same amount of MetAP2 inhibitor subcutaneously administered.

Disclosed methods of treating obesity e.g by non-parenterally or parenterally administering a MetAP2 inhibitor, may result in decreased body fat and a substantial maintenance of muscle mass in said subject. In certain embodiments, upon administration, fat oxidation is enhanced in a subject as compared to a subject on a restricted food intake diet alone. For example, provided herein is a method of decreasing body fat in an overweight or obese subject in need thereof, comprising administering a therapeutically effective amount of a MetAP2 inhibitor to said subject resulting in body fat reduction, and wherein said subject substantially maintains muscle mass during the body fat reduction. Such a subject may retain substantially more muscle mass as compared to body fat reduction in a subject using an energy restricted diet alone.

In some embodiments, disclosed methods, upon administration of a disclosed compound e.g. daily or weekly, for about 3, 4, 5 or 6 months or more may result in at least a 5%, 10%, 20%, or 30%, or more weight loss based on the subject's original weight. In an embodiment, weight loss following treatment with therapeutically effective doses of MetAP2 inhibitors may substantially cease once a subject attains a normal body composition. Without being limited to an theory, this may be due to reliance of the mechanism on re-establishing tone of adrenergic signal transduction in tissues such as fat, liver, and/or skeletal muscle.

In an embodiment, provided herein is a method of maintaining a specified weight in a formerly obese subject, comprising administering a therapeutically effective amount of a a disclosed compound to said subject.

Also provided herein is a method for controlling or preventing hepatic steatosis in an obese subject being treated for obesity, comprising administering a therapeutically effective amount of a a disclosed compound to said subject, in another embodiment, a method for improving liver function in an obese subject is provided, comprising administering a therapeutically effective amount of a a disclosed compound to said subject. For example, a method of restoring normal metabolic action in an obese subject in need thereof is provided, comprising administering a therapeutically effective amount of a a disclosed compound to said subject. In an embodiment, a method of reducing weight of a subject in a subject in need thereof is provided comprising administering a therapeutically effective amount of a a disclosed compound to said subject wherein the metabolic rate of the subject is not substantially reduced as compared to the metabolic rate of a diet only subject on an energy restricted diet alone. In a different embodiment, a method of restoring and/or maintaining thyroid hormone concentrations in an obese subject is provided, comprising administering a therapeutically effective amount of a a disclosed compound to said subject.

In an embodiment, a method of improving exercise capacity in a subject in need thereof is provided that comprises administering a therapeutically effective amount of a a disclosed compound to said subject.

Also provided herein is a method of activating brown fat function in a subject in need thereof, comprising administering a therapeutically effective amount of a disclosed compound to said subject.

Contemplated herein is a method of reducing the amount or frequency of administering supplemental insulin in a subject suffering from type 2 diabetes, comprising administering a therapeutically effective amount of a a disclosed, compound to said subject. Such treatment may be directed to an obese or non-obese subject.

In an embodiment, a method for improving surgical outcome in an obese subject in need thereof by reducing weight of said subject is provided comprising administering a therapeutically effective amount of a a disclosed compound to said subject before non-acute surgery, thereby reducing liver and/or abdominal fat in said subject and improving surgical outcome. Such surgeries may include bariatric surgery, cardiovascular surgery, abdominal surgery, or orthopedic surgery.

In addition to being overweight or obese, a subject can further have an overweight- or obesity-related co-morbidities, i.e., diseases and other adverse health conditions associated with, exacerbated by, or precipitated by being overweight or obese. Because being overweight or obese is associated with other adverse health conditions or co-morbidities, for example diabetes, administering a disclosed compound brings a benefit in ameliorating, arresting development of or, in some cases, even eliminating, these overweight- or obesity-related conditions or co-morbidities. In some embodiments, methods provided herein may further include administering at least one other agent that is directed to treatment of these overweight- or obesity-related conditions.

Contemplated other agents include those administered to treat type 2 diabetes such as sulfonylureas (e.g., chlorpropamide, glipizide, glyburide, glimepiride); meglitinides (e.g., repaglinide and nateglinide); biguanides (e.g., metformin); thiazolidinediones (rosiglitazone, troglitazone, and pioglitazones; glucagon-like 1 peptide mimetics (e.g. exenatide and liraglutide; sodium-glucose cotransporter inhibitors (e.g., dapagliflozin), renin inhibitors, and alpha-glucosidase inhibitors (e.g., acarbose and meglitol), and/or those administered to treat cardiac disorders and conditions, such hypertension, dyslipidemia, ischemic heart disease, cardiomyopathy, cardiac infarction, stroke, venous thromboembolic disease and pulmonary hypertension, which have been linked to overweight or obesity, for example, chlorthalidone; hydrochlorothiazide; indapamide, metolazone; loop diuretics (e.g., bumetanide, ethacrynic acid, furosemide, lasix, torsemide); potassium-sparing agents (e.g., amiloride hydrochloride, spironolactone, and triamterene); peripheral agents (e.g., reserpine); central alpha-agonists (e.g., clonidine hydrochloride, guanabenz acetate, guanfacine hydrochloride, and methyldopa); alpha-blockers (e.g., doxazosin mesylate, prazosin hydrochloride, and terazosin hydrochloride); beta-blockers (e.g., acebutolol, atenolol, betaxolol, nisoprolol fumarate, carteolol hydrochloride, metoprolol tartrate, metoprolol succinate, Nadolol, penbutolol sulfate, pindolol, propranolol hydrochloride, and timolol maleate); combined alpha- and beta-blockers (e.g., carvedilol and labetalol hydrochloride); direct vasodilators (e.g., hydralazine hydrochloride and minoxidil); calcium antagonists (e.g., diltiazem hydrochloride and verapamil hydrochloride); dihydropyridines (e.g., amlodipine besylate, felodipine, isradipine, nicardipine, nifedipine, and nisoldipine); ACE inhibitors (benazepril hydrochloride, captopril, enalapril maleate, fosinopril sodium, lisinopril, moexipril, quinapril hydrochloride, ramiprii, trandolapril); angiotensin II receptor blockers (e.g., losartan potassium, valsartan, and Irbesartan); and combinations thereof, as well as statins such as mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin, typically for treatment of dyslipidemia.

Other agents that may be co-administered (e.g. sequentially of simultaneously) include agents administered to treat ischemic heart disease including statins, nitrates (e.g., Isosorbide Dinitrate and Isosorbide Mononitrate), beta-blockers, and calcium channel antagonists, agents administered to treat cardiomyopathy including inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers, agents administered to treat cardiac infarction including ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase), agents administered to treat strokes including anti-platelet agents (e.g., Aspirin, Clopidogrel, Dipyridamole, and Ticlopidine), anticoagulant agents (e.g., Heparin), and thrombolytic agents, agents administered to treat various thromboembolic disease including anti-platelet agents, anticoagulant agents, and thrombolytic agents, agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil, agents administered to treat asthma include bronchodilators, anti-inflammatory agents, leukotriene blockers, and anti-Ige agents. Particular asthma agents include Zafirlukast, Flunisolide, Triamcinolone, Beclomethason, Terbutaline, Fluticasone, Formoterol, Beclomethasone, Salmeterol, Theophylline, and Xopenix, agents administered to treat sleep apnea include Modafinil and amphetamines, agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents, agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g., glucosmine and chondroitin sulfate), and artificial joint fluid, agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax), agents administered to treat polycystic ovary syndrome include insulin-sensitizers, combinations of synthetic estrogen and progesterone, Spironolactone, Eflornithine, and Clomiphene, agents administered to treat erectile dysfunction include phosphodiesterese inhibitors (e.g., Tadalafil, Sildenafil citrate, and Vardenafil), prostaglandin E analogs (e.g., Alprostadil), alkaloids (e.g., Yohimbine), and testosterone, agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropine, Human Chorionic Gonadotropia (HCG), Human Menopausal Gonadotropia (HmG), progesterone, recombinant follicle stimulating hormone (FSH), Urofollitropin, Heparin, Follitropin alfa, and Follitropin beta, agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic, agents administered to treat depression include serotonin reuptake inhibitors (e.g., Fluoxetine, Escitalopram, Citalopram, Paroxetine, Setraline, and Venlafaxine); tricyclic antidepressants (e.g., Amitriptyline, Iprindole, Lofepramine, Nortryptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butryrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate), agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers, and other weight loss agents, including serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, and topamax.

In some embodiments, contemplated methods may further comprising assessing one or more indices of on-going weight loss, e.g. the ketone body production level in a subject; and optionally adjusting the amount administered; thereby optimizing the therapeutic efficacy of said MetAP2 inhibitor.

Administration and Formulation

Pharmaceutical compositions having compounds disclosed herein can be administered in the form of a free acid. Alternatively, a salt can be prepared by reacting compounds disclosed herein with a suitable base. Pharmaceutically acceptable salts illustratively include those that can be made using the following bases; ammonia, L-arginine, benethamine, benzathene, betaine, bismuth, calcium hydroxide, choline, deanol, diethanolamine, diethylamine, 2-(diethylamino)ethanol, ethylenediamine, N-methylglucamine, hydrobamine, 1 H-imidazole, lysine, magnesium hydroxide, 4-(2-hydroxyethyl)morpholine, piperazine, potassium hydroxide, 1-(2-hydroxyethyl)pyrrolidine, sodium hydroxide, triethanolamine, zinc hydroxide, diclyclohexlamine, or any other electron pair donor (as described in Handbook of Pharmaceutical Salts. Stan & Wermuth, VHCA and Wiley, Uchsenfurt-Hohestadt Germany. 2002). Esters disclosed herein may be prepared by reacting compounds disclosed herein with the appropriate acid under standard esterification conditions described in the literature (Houben-Weyl 4th Ed. 1952. Methods of Organic Synthesis). Suitable esters include ethyl methanoate, ethyl ethanoate, ethyl propanoate, propyl methanoate, propyl ethanoate, and methyl butanoate.

Compounds disclosed herein may be administered using any amount and any route of administration effective for treating a subject having an overweight or obese condition without substantially reducing lean body mass of the subject. Thus, the expression "amount effective for treating a subject having an overweight or obese condition", as used herein, refers to a pharmaceutical composition having a sufficient amount of compounds disclosed herein, or salts or esters thereof, to beneficially result in weight loss without deleterious side effects, such as substantial reduction of lean body mass of the subject.

Dosage and administration are adjusted to provide sufficient levels of compounds disclosed herein, or salts or esters thereof, to maintain the desired effect. Additional factors that may be taken into account include the severity of the disease state, e.g., overweight, obese, or morbidly obese; age, and gender of the subject; diet, time and frequency of administration; route of administration; drug combinations; reaction sensitivities; and tolerance/response to therapy. Long acting pharmaceutical compositions might be administered hourly, twice hourly, every three to four hours, daily, twice daily, every three to four days, every week, or once every two weeks depending on half-life and clearance rate of the particular composition.

Therapeutic efficacy and toxicity of compound disclosed herein, or salts or esters thereof, can be determined by standard pharmaceutical procedures. For example, therapeutic efficacy and toxicity can be determined by minimal efficacious dose or NOAEL (no observable adverse effect level). Alternatively, an ED50 (the dose is therapeutically effective in 50% of the population) and LD50 (the dose is lethal to 50% of the population) can be determined in cell cultures or experimental animals. The dose ratio of toxic to therapeutic effects is the therapeutic index, and it can be expressed as the ratio, LD50/ED50. Pharmaceutical compositions that exhibit large therapeutic indices are preferred.

Compounds disclosed herein, or salts or esters thereof, may be formulated in dosage unit form for ease of administration and uniformity of dosage. In general, the total daily usage of the compositions disclosed herein will be decided by the attending physician within the scope of sound medical judgment. The therapeutically effective dose can be estimated initially either in cell culture assays or in animal models, as provided herein, usually mice, hut also potentially from rats, rabbits, dogs, or pigs. The animal model provided herein is also used to achieve a desirable concentration and total dosing range and route of administration. Such information can then be used to determine useful doses and routes for administration in humans.

Contemplated herein are formulations suitable for non-parenteral administration of a disclosed compound. For example, in certain embodiments, a subject may have a lower systemic exposure (e.g. at least about 2, 3, 5, 10, 20, or at least about 30% less systemic exposure) to the non-parenterally administered (e.g. oral administration) of a disclosed compound as compared to a subject parenterally administered (e.g. subcutaneously) the same dose of the MetAP2 inhibitor.

Contemplated non-parenteral administration include oral, buccal, transdermal (e.g. by a dermal patch), topical, inhalation, or sublingual administration, or e.g., ocular, pulmonary, nasal, rectal or vaginal administration. Contemplated parenteral administration includes subcutaneous, intravenous, intramuscular or intraperitoneal administration.

In another embodiment, provided herein, are effective dosages, e.g. a dally dosage of a a disclosed compound, that may not substantially modulate or suppress angiogenesis. For example, provided here are methods that include administering doses of a disclosed compound that are effective for weight loss, but are significantly smaller doses than that necessary to modulate and/or suppress angiogenesis (which may typically require about 12.5 mg/kg to about 50 mg/kg or more). For example, contemplated dosage of a disclosed compound in the methods described herein may include administering about 25 mg/day, about 10 mg/day, about 5 mg/day, about 3 mg/day, about 2 mg/day, about 1 mg/day, about 0.75 mg/day, about 0.5 mg/day, about 0.1 mg/day, about 0.05 mg/day, or about 0.01 mg/day. For example, an effective amount of the drug for weight loss in a subject may be about 0.0001 mg/kg to about 25 mg/kg of body weight per day. For example, a contemplated dosage may from, about 0.001 to 10 mg/kg of body weight per day, about 0.001 mg/kg to 1 mg/kg of body weight per day, about 0.001 mg/kg to 0.1 mg/kg of body weight per day or about 0.005 to about 0.04 mg/kg or about 0.005 to about 0.049 mg/kg of body weight a day.

Contemplated methods may include administration of a composition comprising a disclosed compound, for example, hourly, twice hourly, every three to four hours, daily, twice dally, 1, 2, 3 or 4 times a week, every three to four days, every week, or once every two weeks depending on half-life and clearance rate of the particular composition or inhibitor.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. For example, when about loss of about 20% body weight, about 30% body weight or more has been achieved. A treatment regimen ran include a corrective phase, during which a a disclosed compound dose sufficient to provide reduction of excess adiposity is administered followed by a maintenance phase, during which a lower dose sufficient to prevent re-development of excess adiposity is administered.

For pulmonary (e.g., intrabronchial) administration, compounds disclosed herein, or a salt or ester thereof, can be formulated with conventional excipients to prepare an inhalable composition in the form of a fine powder or atomizable liquid.

For ocular administration, compounds disclosed herein, or a salt or ester thereof, can be formulated with conventional excipients in the form of eye drops or an ocular implant. Among excipients useful in eye drops are viscosifying or gelling agents, to minimize loss by lacrimation through improved retention in the eye.

Liquid dosage forms for oral or other systemic administration include, but are not limited to, pharmaceutically acceptable emulsions, microemulsion, solutions, suspensions, syrups and elixirs. In addition to the active agent(s), the liquid dosage forms may contain inert diluents commonly used in the art such as, for example, water or other solvents, solubilizing agents and emulsifiers such as ethyl, alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration, are achieved with aqueous drops, a mist, an emulsion, or a cream.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water. Ringer's solution, U.S.P. and isotonic sodium chloride solution. In addition, sterile, fixed oils are conventionally employed as a solvent or suspending medium.

Compositions for rectal or vaginal administration may be suppositories which can be prepared by mixing the active agent(s) disclosed herein with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. Alternatively, formulations suitable for use with the methods disclosed herein are incorporated into chewable tablets, crushable tablets, tablets that dissolve rapidly in within the mouth, or mouthwash. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well, known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waves.

In addition to being overweight or obese, a subject can further have an overweight- or obesity-related co-morbidities, i.e., diseases and other adverse health conditions associated with, exacerbated by, or precipitated by being overweight or obese. Thus, a method of treating a subject having an overweight- or obesity-related condition is provided herein, the method involving administering to the subject a therapeutically effective amount of compounds disclosed herein, or a salt or ester thereof, such that the amount administered does not substantially reduce lean body mass of the subject.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15).

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss.

Respiratory disorders and conditions such as obesity-hypoventilation syndrome, asthma, and obstructive sleep apnea, have been linked to being overweight or obese, Elamin (Chest (2004) 125:1972-1974) discusses a link between being overweight or obese and asthma. Kressler et al. (Eur Respir J (1996) 9:787-794) discusses a link between being overweight or obese and obstructive sleep apnea. Hepatic disorders and conditions, such as nonalcoholic tatty liver disease, have been linked to being overweight or obese. Tolman et al. (Ther Clin Risk Manag (2007) 6:1153-1163) discusses a link between being overweight or obese and nonalcoholic fatty liver disease.

Because being overweight or obese is associated with the above conditions, administering pharmaceutical compositions having compounds disclosed herein bring a benefit in ameliorating, arresting development of or, in some cases, even eliminating, these overweight- or obesity-related conditions.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1

Orally Administered Compounds Having MetAP-2 Inhibitory Cores Cause Weight Loss in Diet-Induced Obese Mice A weight loss study was conducted in obese mice. The mice in this study were not genetically obese, but prior to and during the study, obesity was induced by a high-fat diet. Twelve week-old C57BL/6NTac mice, maintained on a 60% fat diet prior to and during the study, were separated into seven groups, eight animals per group. Average body weight of the mice was approximately 47 g at the start of the study.

Each of six groups was orally administered 1.0 mg/kg of a compound (fumagillin and compounds B, C, D, E, F and G), in 10% gelucire in deionised water. Compounds B-G are as follows:

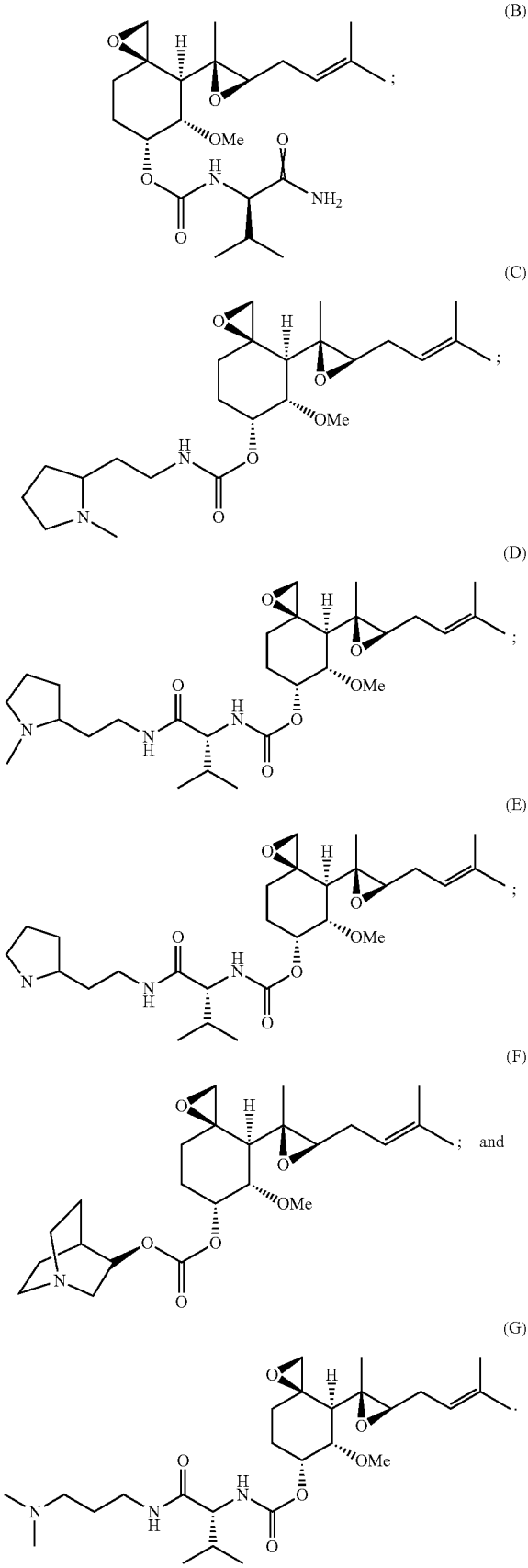

Each of these six groups was administered a different compound. One group was orally administered fumagillin at 1.0 mg/kg (ZGN-201) in 10% gelucire in deionised water, and one group was administered 10% gelucire in deionised water (vehicle). Mice received administrations once a day for 7 days.

Data show that mice administered fumagillin lost the most weight over the course of the 8 days (the FIGURE). Mice in groups B, C, D, and E also lost weight over the course of the 8 days, with mice in group C losing the most weight of these four groups (the FIGURE). (Data analyzed by ANCOVA with body weight on Day 1 as covariate followed by multiple tests against vehicle group: *$p<0.05$; $p<0.01$, *$p<0.001$.)

What is claimed is:

1. A method of treating a subject having an overweight or obese condition, the method comprising: administering to the subject in need thereof, a therapeutically effective amount of a pharmaceutical composition comprising a compound of Formula C-D wherein C is represented by:

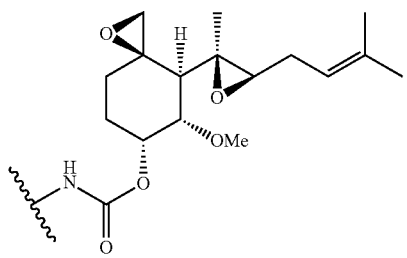

and D is represented by:

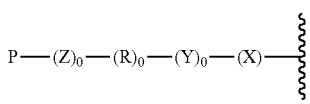

wherein:
Z, R and Y are not present;
X is $C_{1-6}$alkyl;
P is a moiety selected from the group consisting of:

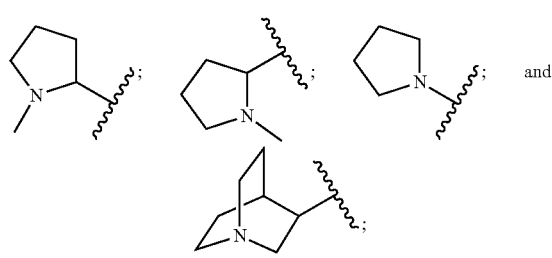

or a pharmaceutically acceptable salt thereof.

2. A method of treating a subject having an overweight or obese condition, the method comprising: administering to the subject a therapeutically effective amount of a pharmaceutical composition comprising a compound selected from the group consisting of:

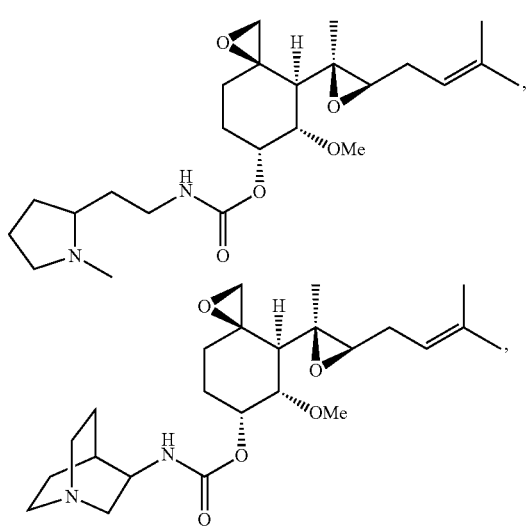

and a pharmaceutically acceptable salt thereof.

3. The method of claim 2, wherein the subject has a Body Mass Index measurement selected from the group consisting of: at least about 25 kg/m$^2$, at least about 30 kg/m$^2$, and at least about 40 kg/m$^2$.

4. The method of claim 2, wherein the pharmaceutical composition is administered non-parenterally.

5. The method of claim 2, wherein the pharmaceutical composition is administered parenterally.

6. The method of claim 2, wherein the pharmaceutical composition is administered subcutaneously.

7. A method for controlling hepatic steatosis in an obese subject being treated for obesity, comprising administering a therapeutically effective amount of a pharmaceutical composition comprising a compound selected from the group consisting of:

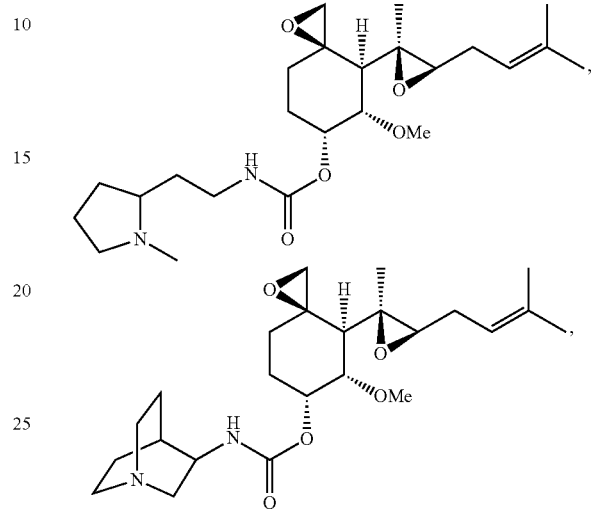

and a pharmaceutically acceptable salt thereof.

* * * * *